US011999696B2

(12) United States Patent
George et al.

(10) Patent No.: US 11,999,696 B2
(45) Date of Patent: Jun. 4, 2024

(54) HETEROCYCLIC AZIDE UNITS AND THEIR USE IN POLYMER COATINGS

(71) Applicant: ILLUMINA CAMBRIDGE LIMITED, Cambridge (GB)

(72) Inventors: Wayne N. George, Ilford (GB); Xiaolin Wu, Cambridge (GB); Andrew A. Brown, Cambridge (GB); Donald Wellings, Runcorn (GB)

(73) Assignee: Illumina Cambridge Limited, Cambridge (GB)

( * ) Notice: Subject to any disclaimer, the term of this patent is extended or adjusted under 35 U.S.C. 154(b) by 739 days.

(21) Appl. No.: 17/257,270

(22) PCT Filed: Dec. 9, 2019

(86) PCT No.: PCT/EP2019/084173
§ 371 (c)(1),
(2) Date: Dec. 30, 2020

(87) PCT Pub. No.: WO2020/126598
PCT Pub. Date: Jun. 25, 2020

(65) Prior Publication Data
US 2021/0284609 A1    Sep. 16, 2021

Related U.S. Application Data

(60) Provisional application No. 62/816,691, filed on Mar. 11, 2019, provisional application No. 62/787,600, filed on Jan. 2, 2019, provisional application No. 62/781,428, filed on Dec. 18, 2018.

(51) Int. Cl.
*C07D 213/75*   (2006.01)
*C07D 207/16*   (2006.01)
*C07D 213/82*   (2006.01)
*C08F 220/56*   (2006.01)

(52) U.S. Cl.
CPC ......... *C07D 213/75* (2013.01); *C07D 207/16* (2013.01); *C07D 213/82* (2013.01); *C08F 220/56* (2013.01); *C08F 2810/50* (2013.01)

(58) Field of Classification Search
CPC .... C07D 213/75; C07D 207/16; C08F 220/56
See application file for complete search history.

(56) References Cited

U.S. PATENT DOCUMENTS

| 2014/0079923 A1 | 3/2014 | George et al. |
| 2014/0106979 A1 | 4/2014 | Lau et al. |
| 2016/0122816 A1 | 5/2016 | Brown et al. |

FOREIGN PATENT DOCUMENTS

| CN | 107076739 A | 8/2017 |
| EP | 2966061 | 1/2016 |
| WO | 2013148189 A1 | 10/2013 |

OTHER PUBLICATIONS

Kehagias, Nikolas, et al., "Stamp replication for thermal and UV nanoimprint lithography using a UV-sensitive silsesquioxane resist", Microelectronic Engineering, vol. 86, Issue 4-6, pp. 776-778, Apr. 2009.
Kuang, Gui-Chao, et al., "Chelation-Assisted, Copper(II)-Acetate-Accelerated Azide-Alkyne Cycloaddition", J. Org. Chem. 2010, 75, 6540-6548, Aug. 31, 2010.
Sallustrau, A., et al., "Scalable and practical synthesis of clickable Cu-chelating azides", Chem. Commun., 2017, 53, 7890, Jun. 5, 2017.
Clark et al., "In situ crosslinked hydrogels formed using Cu(I)-free Huisgen cycloaddition reaction", Polymer International, vol. 58, Issue 10, Oct. 2009, pp. 1190-1195, https://doi.org/10.1002/pi.2650 (Published online Aug. 5, 2009), 2009.

*Primary Examiner* — Catherine S Branch
(74) *Attorney, Agent, or Firm* — Dierker & Kavanaugh, P.C.

(57) ABSTRACT

Described herein are heterocyclic azide-containing monomer units, copolymers comprising such heterocyclic azide-containing monomer units, substrate-bound copolymers, and oligonucleotide-bound copolymers, methods for making such copolymers and reacting them with a substrate and/or oligonucleotide, and methods of using such copolymers for immobilization of oligonucleotides to a substrate, for example for use in DNA sequencing or other diagnostic applications.

20 Claims, No Drawings
Specification includes a Sequence Listing.

HETEROCYCLIC AZIDE UNITS AND THEIR USE IN POLYMER COATINGS

CROSS-REFERENCE TO RELATED APPLICATIONS

This application is a national stage entry under 35 U.S.C. § 371 of International application No. PCT/EP2019/084173, filed Dec. 9, 2019, which itself claims the benefit of: U.S. Provisional Patent Application No. 62/781,428, filed Dec. 18, 2018 and entitled "Heterocyclic Azide Units in Polymer Coatings"; U.S. Provisional Patent Application No. 62/787,600, filed Jan. 2, 2019 and entitled "Heterocyclic Azide Units in Polymer Coatings"; and U.S. Provisional Patent Application No. 62/816,691, filed Mar. 11, 2019 and entitled "Heterocyclic Azide Units in Polymer Coatings", each of which is incorporated by reference in its entirety.

REFERENCE TO SEQUENCE LISTING

The Sequence Listing submitted herewith via EFS-Web is hereby incorporated by reference in its entirety. The name of the file is ILI211AUS_IP-1807-US_Sequence_Listing_ST25.txt, the size of the file is 1130 bytes, and the date of creation of the file is Dec. 30, 2020.

BACKGROUND

Polymer-coated substrates are used in many technological applications. For example, implantable medical devices can be coated with biologically inert polymers. In another example, polymer-coated substrates are used for the preparation and/or analysis of biological molecules. Molecular analyses, such as certain nucleic acid sequencing methods, rely on the attachment of nucleic acid strands to a polymer-coated surface of a substrate. The sequences of the attached nucleic acid strands can then be determined by a number of different methods that are known in the art.

In certain sequencing processes, such as sequencing-by-synthesis (SBS), a surface of a substrate, such as a flow cell, is coated with a polymer to which primers (single stranded DNA or ssDNA) are then grafted. In array methods, beads are coated with polymers that likewise are functionalized to capture target oligonucleotides.

The polymer surfaces (and their preparation) are generally compatible with a wide range of sequencing and detection processes, including different chemical conditions, temperatures, optical detection methods, capture moiety densities, and other parameters, and are generally stable under various storage and shipping conditions. Certain polymer materials used in these molecular biology approaches employ pendant azido groups that are reacted in a copper-mediated cycloaddition reaction with alkene or alkyne groups on the surface of a substrate and/or oligonucleotides to be grafted. Residual copper, however, can have cytotoxic effects in biologically-relevant environments. With respect to DNA sequencing applications, in some instances copper can damage DNA, thereby reducing sequencing yield and data quality. In addition, often copper-catalyzed reactions are copper-intensive, and therefore are expensive, and may not run efficiently or quickly enough to ensure adequate polymer attachment and localization on a substrate surface. Thus, there is a need for surface polymer coatings with improved properties, such as increased reaction efficiency and that lead to reduced residual copper.

SUMMARY

Examples provided herein are related to polymers comprising heterocyclic azide units, optionally with oligonucleotides grafted thereto, substrates with the polymers attached thereto, and use of the polymers and substrates in applications such as molecular biology methods such as DNA sequencing and other diagnostic applications. Methods of preparing the heterocyclic azide polymers and the substrates and methods of using the compositions are also disclosed.

Provided in some examples herein are monomers and copolymers that employ heterocyclic azido groups that react efficiently in cycloaddition reactions with reduced copper loading and thus lower residual copper.

In one aspect, provided herein is a compound of formula (I)

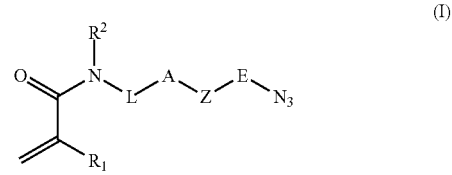

wherein $R^1$ is H or $C_{1-4}$ alkyl; $R^2$ is H or $C_{1-4}$ alkyl; L is a linker comprising a linear chain comprising 2 to 20 atoms selected from the group consisting of carbon, oxygen, and nitrogen and optional substituents on the carbon and any nitrogen atoms in the chain; E is a linear chain comprising 1 to 4 atoms selected from the group consisting of carbon, oxygen and nitrogen, and optional substituents on the carbon and any nitrogen atoms in the chain; A is an N substituted amide having formula

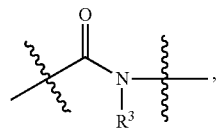

wherein $R^3$ is H or $C_{1-4}$ alkyl; and Z is a nitrogen containing heterocycle.

In some examples E may be optionally substituted $C_{1-4}$ alkylene.

In some examples the compound of formula (I) may be a compound of formula (Ia)

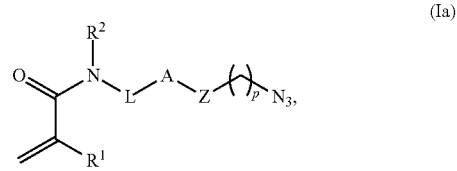

wherein p is 1, 2, 3 or 4.

In some examples, the nitrogen containing heterocycle may comprise a 6 membered ring. Illustratively, A and E (for example the alkylene azido group) are bonded at positions 2 and 5 of the 6 membered ring. In other examples, the nitrogen containing heterocycle comprises a 5 membered ring.

Additionally, or alternatively, the nitrogen containing heterocycle optionally is aromatic, or optionally is saturated.

Additionally or alternatively, the compound is optionally of formula (Ib)

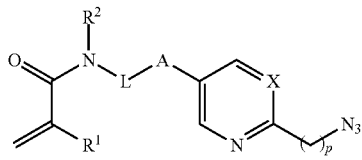
(Ib)

wherein X is CH or N.

Alternatively, the compound is optionally of formula (Ic)

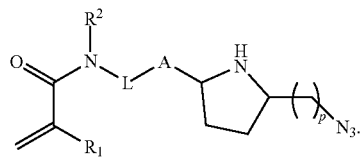
(Ic)

Alternatively, the compound is optionally of formula (Id)

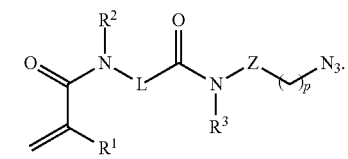
(Id)

Alternatively, the compound is optionally of formula (Ie)

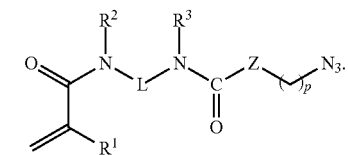
(Ie)

In another example, the compound is of formula (If)

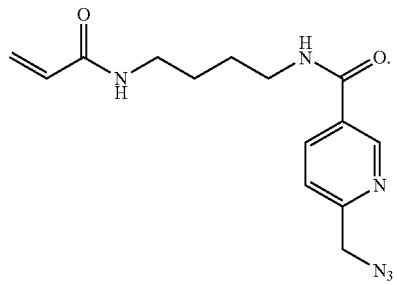
(If)

In another example, the compound is of formula (Ig)

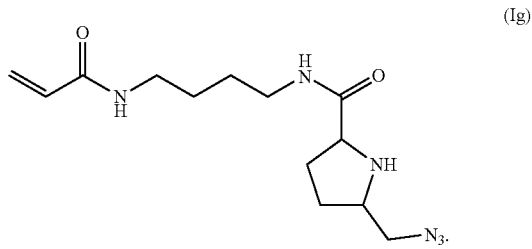 [SMILES: C=CC(=O)NCCCCNC(=O)C1CCC(CN=[N+]=[N-])N1]
(Ig)

In another example, the compound is of formula (Ih)

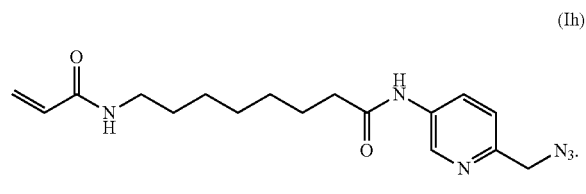 [SMILES: C=CC(=O)NCCCCCCCC(=O)Nc1ccc(CN=[N+]=[N-])nc1]
(Ih)

In another example, the compound is of formula (Ij)

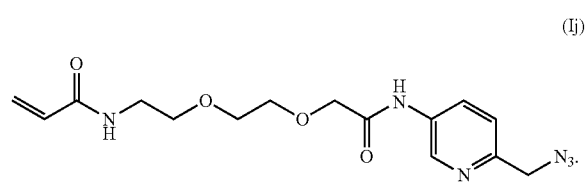 [SMILES: C=CC(=O)NCCOCCOCC(=O)Nc1ccc(CN=[N+]=[N-])nc1]
(Ij)

In some examples, the compound is of formula (Ik)

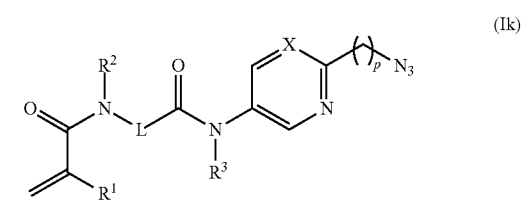
(Ik)

wherein X is CH or N.

Illustratively, the compound of Formula (Ik) is a compound of Formula (Im):

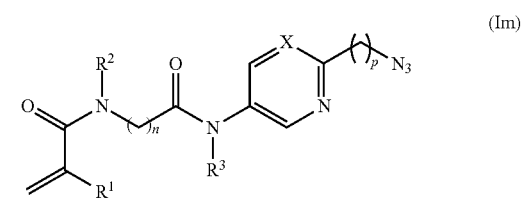
(Im)

wherein n is an integer from 2 to 20.

In another aspect, provided herein is a copolymer comprising a recurring monomer unit of Formula (II)

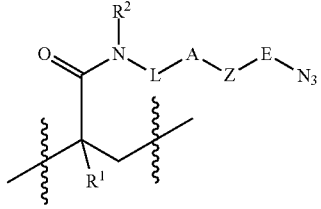
(II)

wherein $R^1$ is H or $C_{1-4}$ alkyl; $R^2$ is H or $C_{1-4}$ alkyl; L is a linker comprising a linear chain comprising 2 to 20 atoms selected from the group consisting of carbon, oxygen, and nitrogen and optional substituents on the carbon and any nitrogen atoms in the chain; E is a linear chain comprising 1 to 4 atoms selected from the group consisting of carbon, oxygen and nitrogen, and optional substituents on the carbon and any nitrogen atoms in the chain; A is an N substituted amide having formula

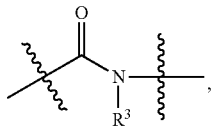

wherein $R^3$ is H or $C_{1-4}$ alkyl; and Z is a nitrogen containing heterocycle; and at least one other recurring monomer unit.

In some examples, the recurring monomer unit of formula (II) is a recurring monomer unit of formula (IIa):

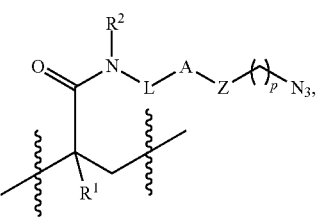
(IIa)

wherein p is 1, 2, 3 or 4.

In some examples, the recurring monomer unit of formula (IIa) is a recurring monomer unit of Formula (IIb), Formula (IIc), Formula (IId), or Formula (IIe):

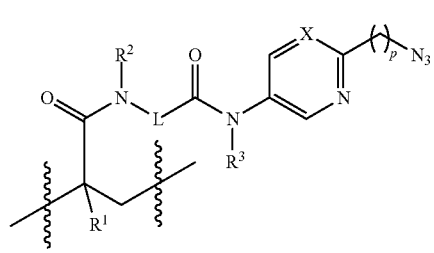
(IIb)

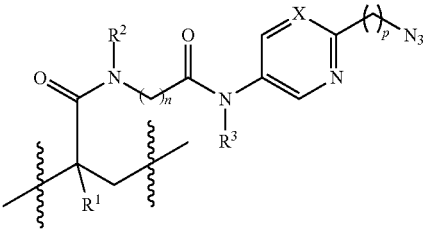
(IIc)

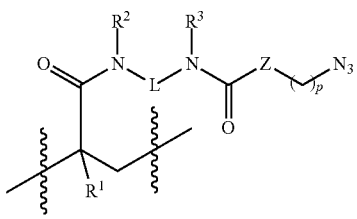
(IId)

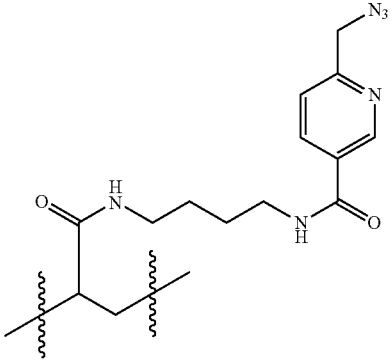
(IIe)

wherein n in Formula (IIc) is an integer from 2 to 20. In some examples, the at least one other recurring monomer unit is a compound of Formula (III):

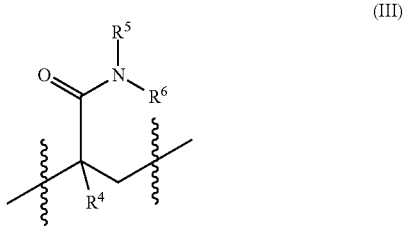
(III)

wherein $R^4$ is H or $C_{1-4}$alkyl; $R^5$ is H or $C_{1-4}$alkyl; and $R^6$ is H or $C_{1-4}$alkyl.

Illustratively, the copolymer comprises a recurring monomer unit of Formula (II), (IIa), (IIb), (IIc), (IId), or (IIe), a recurring monomer unit of Formula (III), and at least one other recurring monomer unit.

In another aspect, provided herein is a substrate-copolymer product formed from reaction of the copolymer as set out above with a substrate. In some examples, the substrate copolymer product is formed by reaction of the azido group of the copolymer with an alkenyl- or alkynyl-containing group on a surface of the substrate.

In another aspect, there is provided herein a structure comprising a copolymer covalently bound to the substrate, wherein the substrate-bound copolymer comprises a recurring monomer unit that is covalently bound to the substrate, wherein the recurring, covalently-bound, monomer unit is a compound of Formula (IV):

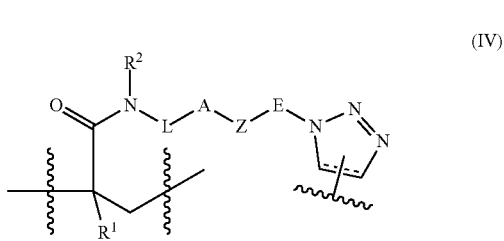

wherein $R^1$ is H or $C_{1-4}$ alkyl; $R^2$ is H or $C_{1-4}$ alkyl; L is a linker comprising a linear chain comprising 2 to 20 atoms selected from the group consisting of carbon, oxygen, and nitrogen and optional substituents on the carbon and any nitrogen atoms in the chain; E is a linear chain comprising 1 to 4 atoms selected from the group consisting of carbon, oxygen and nitrogen, and optional substituents on the carbon and any nitrogen atoms in the chain; A is an N substituted amide having formula

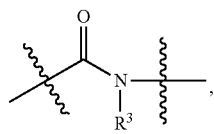

wherein $R^3$ is H or $C_{1-4}$ alkyl; Z is a nitrogen containing heterocycle; ----- is a single or double bond; and the triazole or triazoline is covalently bound, directly or indirectly through a linker, through one or both triazole/triazoline ring carbon atoms to the substrate.

In some examples, the recurring, covalently-bound monomer unit is a compound of formula (IVa):

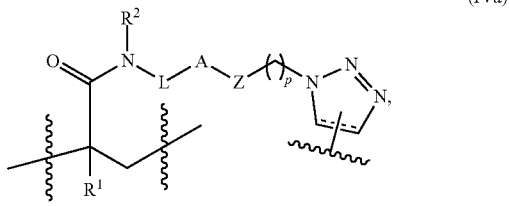

wherein p is 1, 2, 3 or 4.

In some examples, the recurring, covalently-bound monomer unit is a compound of Formula (V):

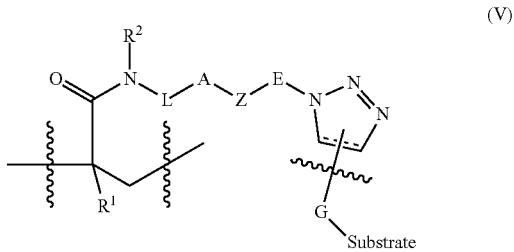

wherein G is a linker between the triazole/triazoline ring and the substrate. In some examples, the recurring, covalently-bound monomer unit is a compound of Formula (Va):

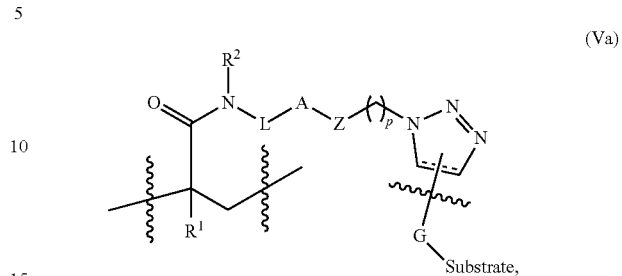

wherein p is 1, 2, 3 or 4.

In some examples, the recurring, covalently-bound, monomer unit is a compound of Formula (IVb), formula (IVc), formula (IVd), or formula (IVe):

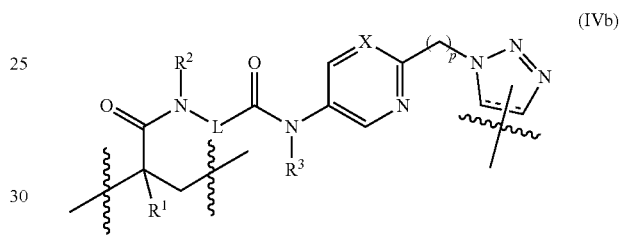

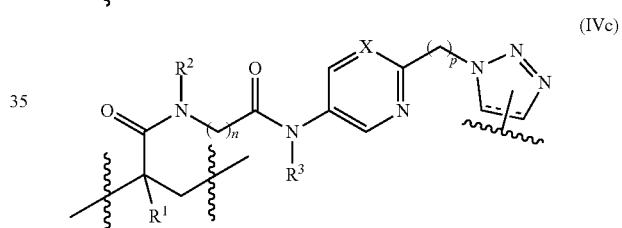

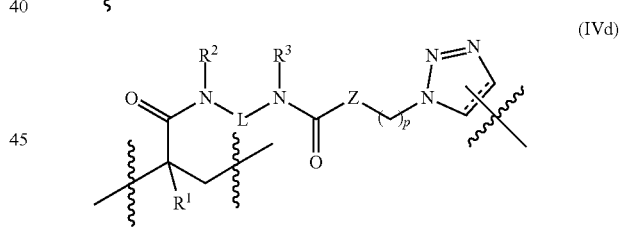

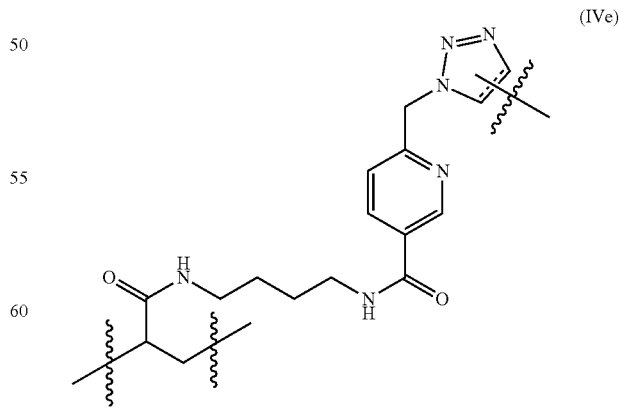

wherein X is CH or N; and n in formula (IVc) is an integer from 2 to 20.

Alternatively or additionally, the recurring, covalently-bound monomer unit is optionally a compound of formula (Vb), formula (Vc), formula (Vd), or formula (Ve):

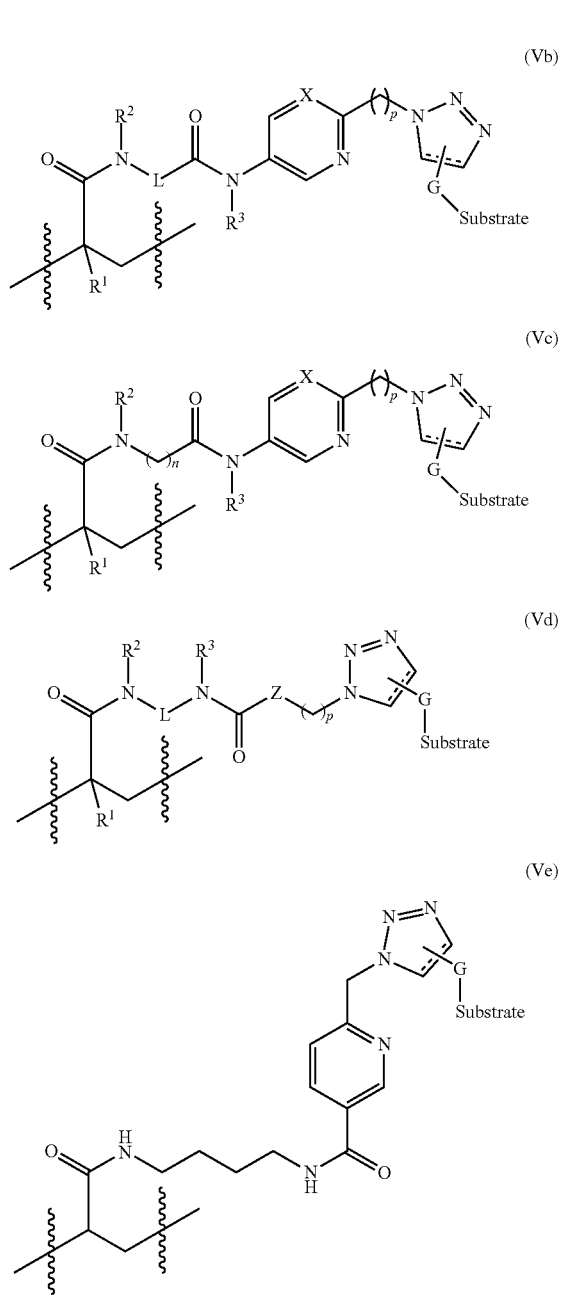

wherein G is a linker between the triazole/triazoline ring and the substrate.

In another aspect, provided herein is a copolymer-oligonucleotide product formed from reaction between the copolymer as set out above and one or more oligonucleotides.

In some examples, the copolymer oligonucleotide product is formed from reaction of the azido group of the copolymer and an alkene- or alkyne-functionalized oligonucleotide.

In another aspect, provided herein is an oligonucleotide bound copolymer, comprising a recurring monomer unit of Formula (IV):

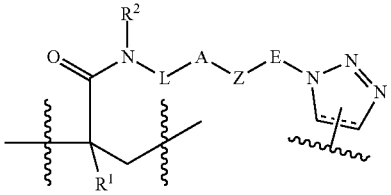

wherein $R^1$ is H or $C_{1-4}$ alkyl; $R^2$ is H or $C_{1-4}$ alkyl; L is a linker comprising a linear chain comprising 2 to 20 atoms selected from the group consisting of carbon, oxygen, and nitrogen and optional substituents on the carbon and any nitrogen atoms in the chain; E is a linear chain comprising 1 to 4 atoms selected from the group consisting of carbon, oxygen and nitrogen, and optional substituents on the carbon and any nitrogen atoms in the chain; A is an N substituted amide having formula

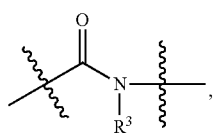

wherein $R^3$ is H or $C_{1-4}$ alkyl; Z is a nitrogen containing heterocycle; ----- is a single or double bond; and the copolymer is covalently bound, directly or indirectly through a linker, through one or both triazole/triazoline ring carbon atoms to the oligonucleotide.

In some examples, the oligonucleotide-bound recurring monomer unit is of Formula (IVa):

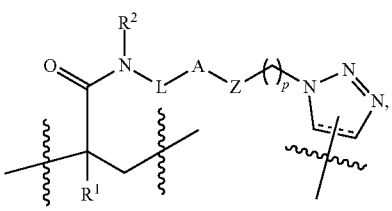

wherein p is 1, 2, 3 or 4.

In some examples, the oligonucleotide-bound recurring monomer unit is of Formula (VI):

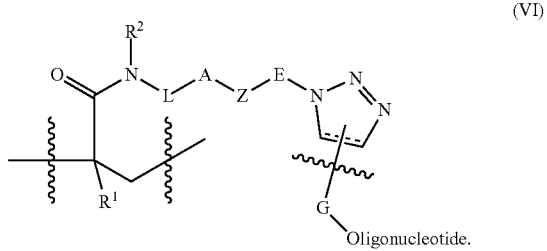

In some examples, the oligonucleotide-bound recurring monomer unit is of formula (VIa):

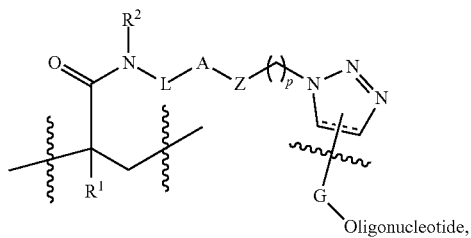

wherein p is 1, 2, 3 or 4.

In some examples, the oligonucleotide-bound recurring monomer unit is of Formula (IVb), formula (IVc), formula (IVd), or formula (IVe):

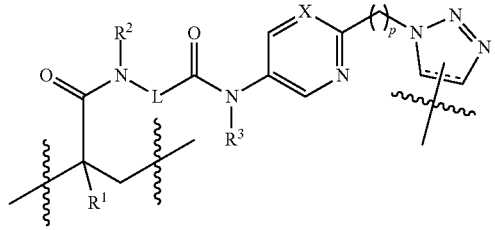

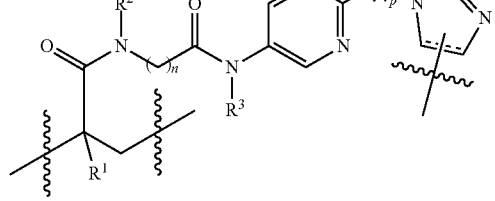

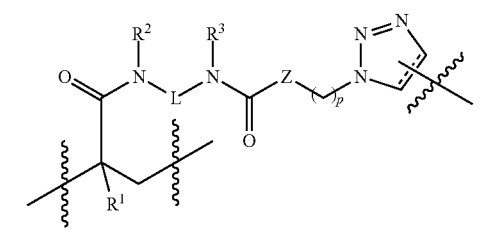

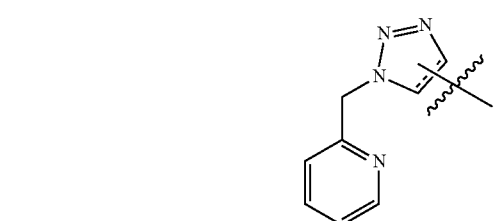

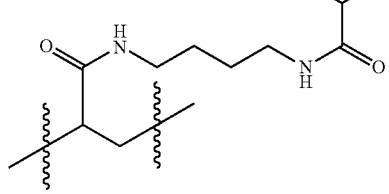

wherein X is CH or N; and n in formula (IVc) is an integer from 2 to 20.

Additionally or alternatively, the oligonucleotide-bound recurring monomer unit is optionally of Formula (VIb), Formula (VIc), Formula (VId), or Formula (VIe):

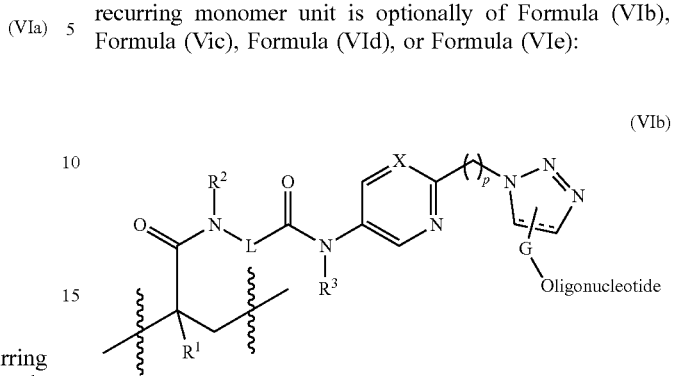

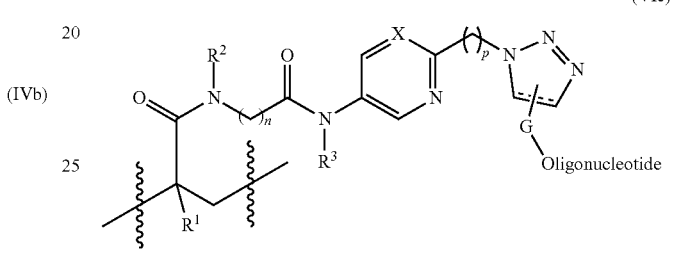

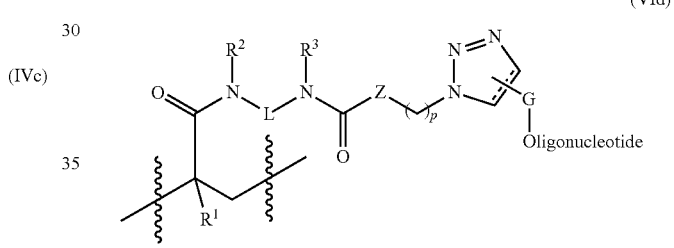

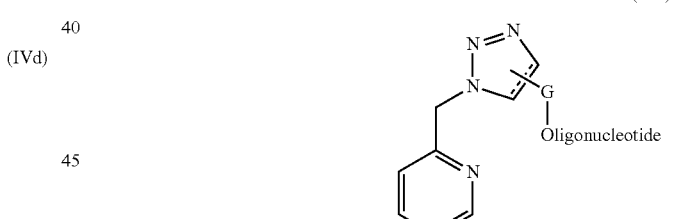

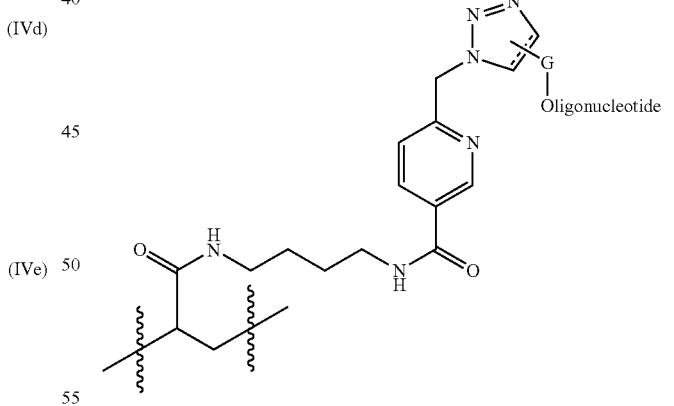

wherein X is CH or N; and n in formula (IVc) is an integer from 2 to 20.

In another aspect, provided herein is a copolymer-substrate-oligonucleotide product formed by reaction of the copolymer according to any statement above with a substrate and one or more oligonucleotides.

In another aspect, provided herein is a method of immobilizing a copolymer according to any statement set out above to a substrate, comprising reacting azido groups of the copolymer with a plurality of alkenyl- or alkynyl-containing functional groups on a surface of the substrate to form covalent bonds between the copolymer and the surface of the substrate.

In another aspect, provided herein is a method of grafting a plurality of oligonucleotides to a copolymer according to any statement set out above, comprising reacting azido groups of the copolymer with the plurality of oligonucleotides. In some examples, the plurality of oligonucleotides comprise alkenyl or alkynyl groups, and the reaction occurs between the azido groups of the copolymer and the alkenyl or alkynyl groups of the oligonucleotides.

In another aspect, provided herein is a method of making a compound of formula (I):

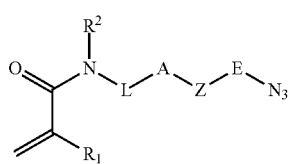

(I)

comprising reacting a compound of Formula (X) with an acrylate of Formula (XI):

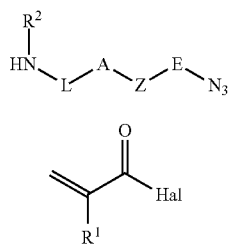

(X)

(XI)

wherein $R^1$ is H or $C_{1-4}$ alkyl; $R^2$ is H or $C_{1-4}$ alkyl; L is a linker comprising a linear chain comprising 2 to 20 atoms selected from the group consisting of carbon, oxygen, and nitrogen and optional substituents on the carbon and any nitrogen atoms in the chain; E is a linear chain comprising 1 to 4 atoms selected from the group consisting of carbon, oxygen and nitrogen, and optional substituents on the carbon and any nitrogen atoms in the chain; A is an N substituted amide having formula

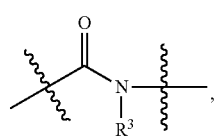

wherein $R^3$ is H or $C_{1-4}$ alkyl; Z is a nitrogen containing heterocycle; and Hal is $C_1$ or F to form the compound of Formula (I).

In another aspect, provided herein is a method of making a compound of Formula (Ik):

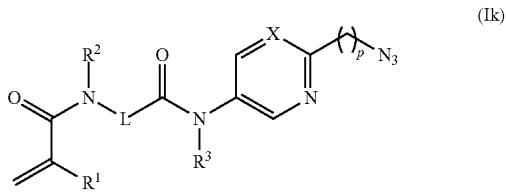

(Ik)

comprising reacting a compound of Formula (Xa):

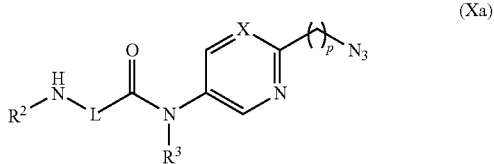

(Xa)

with an acrylate of Formula (XI):

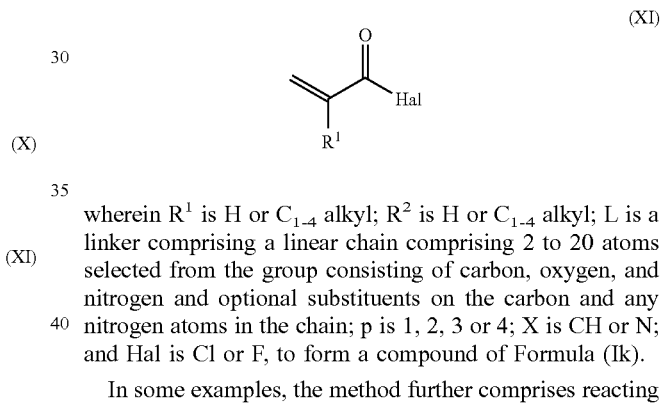

(XI)

wherein $R^1$ is H or $C_{1-4}$ alkyl; $R^2$ is H or $C_{1-4}$ alkyl; L is a linker comprising a linear chain comprising 2 to 20 atoms selected from the group consisting of carbon, oxygen, and nitrogen and optional substituents on the carbon and any nitrogen atoms in the chain; p is 1, 2, 3 or 4; X is CH or N; and Hal is Cl or F, to form a compound of Formula (Ik).

In some examples, the method further comprises reacting a compound of Formula (XII):

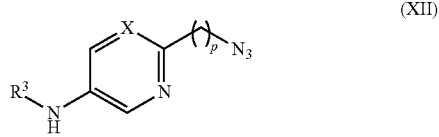

(XII)

with a compound of Formula (XIII):

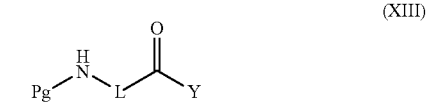

(XIII)

wherein Pg is H or an amino protecting group; and Y is —OH or —Cl; to form the compound of Formula (Xa).

In another aspect, provided herein is a method of making a compound of Formula (Ik) comprising reacting a compound of Formula (XIV):

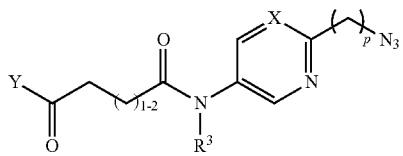

wherein Y is —OH or —Cl; with a compound of Formula (XV):

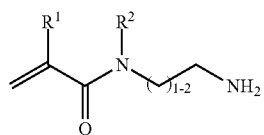

to form the compound of Formula (Ik)

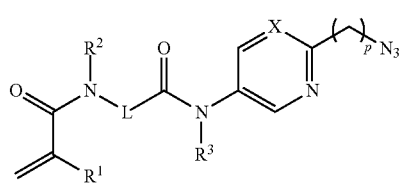

wherein $R^1$ is H or $C_{1-4}$ alkyl; $R^2$ is H or $C_{1-4}$ alkyl; L is a linker comprising a linear chain comprising 6 to 8 atoms selected from the group consisting of carbon, oxygen, and nitrogen and optional substituents on the carbon and any nitrogen atoms in the chain; p is 1, 2, 3 or 4; and X is CH or N.

In some examples, the method further comprises reacting a compound of Formula (XII) with a cyclic anhydride to form the compound of Formula (XIV).

Some examples provided by the present application are directed to a compound of Formula (Ik):

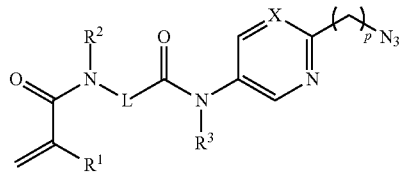

wherein $R^1$ is H or $C_{1-4}$alkyl; $R^2$ is H or $C_{1-4}$alkyl; $R^3$ is H or $C_{1-4}$alkyl; X is CH or N; p is 1, 2, 3, or 4; and L is a linker with a linear chain consisting of 2 to 20 atoms selected from the group consisting of carbon, oxygen, and nitrogen and optional substituents on the carbon and nitrogen atoms in the chain.

In some aspects, a compound of Formula (Ik) is a compound of Formula (Im):

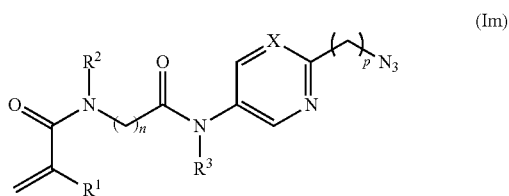

wherein $R^1$ is H or $C_{1-4}$alkyl; $R^2$ is H or $C_{1-4}$alkyl; $R^3$ is H or $C_{1-4}$alkyl; X is CH or N; p is 1, 2, 3, or 4; and n is an integer from 2 to 20.

Some examples provided by the present application are directed to a copolymer comprising a recurring monomer unit of Formula (IIb), Formula (IIc), Formula (IId), or Formula (IIe):

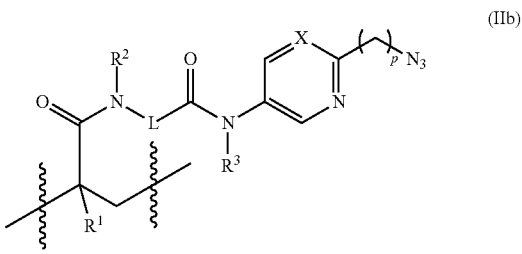

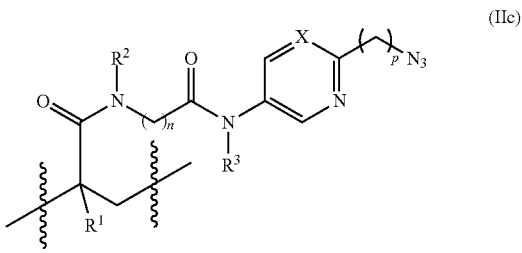

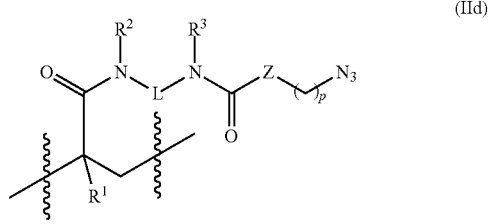

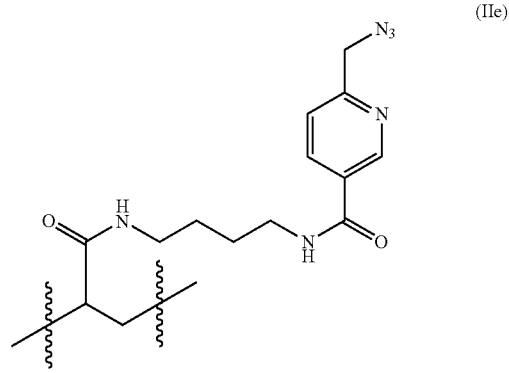

wherein $R^1$ is H or $C_{1-4}$alkyl; $R^2$ is H or $C_{1-4}$alkyl; $R^3$ is H or $C_{1-4}$alkyl; X is CH or N; p is 1, 2, 3, or 4; and L in Formula (I%) is a linker with a linear chain consisting of 2 to 20 atoms selected from the group consisting of carbon, oxygen, and nitrogen and optional substituents on the carbon and nitrogen atoms in the chain; and n in Formula (IIc) is an integer from 2 to 20; and at least one other recurring monomer unit.

The copolymer may be linear, branched, or cross-linked. The recurring units may be present in any arrangement within the copolymer, such as block, alternating, or random. The copolymer may further comprise one or more additional recurring monomer units.

In some aspects, the copolymer comprises a recurring monomer unit of Formula (II), (IIa), (IIb), (IIc), (IId), or (IIe) and a recurring monomer unit of Formula (III):

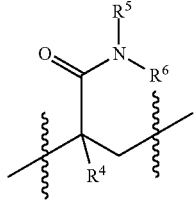
(III)

wherein $R^4$ is H or $C_{1-4}$alkyl; Ie is H or $C_{1-4}$alkyl; and $R^6$ is H or $C_{1-4}$alkyl.

In some aspects, the copolymer comprises a recurring monomer unit of Formula (II), (IIa), (IIb), (IIc), (IId), or (IIe), a recurring monomer unit of Formula (III), and at least one other recurring monomer unit.

Some examples provided in the present application are directed to a substrate having a copolymer as described herein covalently bound to a substrate. In some examples, the covalent attachment is made by reaction of the azido group of a monomer unit of Formula (II), (IIa), (IIb), (IIc), (IId), or (IIe) with an alkenyl- or alkynyl-containing group on a surface of the substrate. Because not all azido groups in a copolymer necessarily would react, such examples are substrate-bound copolymers comprising a recurring monomer unit of Formula (II), (IIa), (IIb), (IIc), (IId), or (IIe). In some examples, the substrate-bound copolymer further comprises a recurring monomer unit that is covalently bound to a substrate. The recurring, covalently-bound, monomer unit is represented by Formula (IVb), Formula (IVc), Formula (IVd), or Formula (IVe):

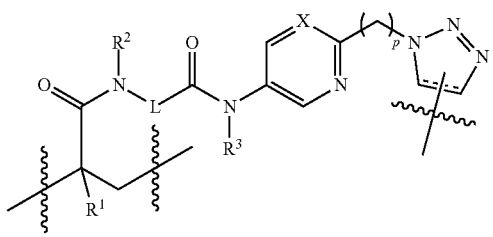
(IVb)

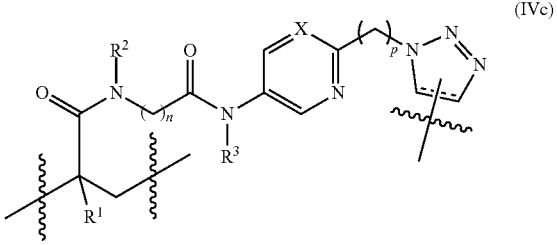
(IVc)

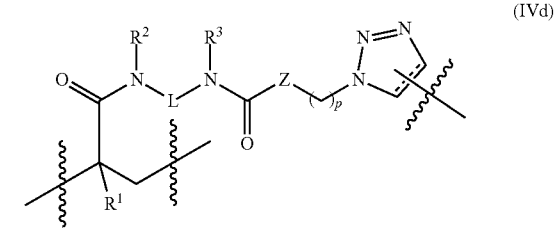
(IVd)

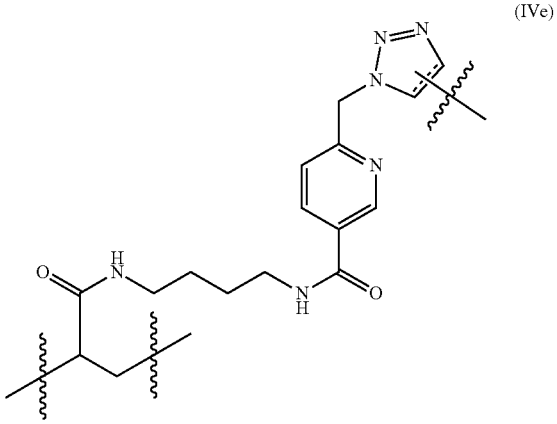
(IVe)

wherein $R^1$, $R^2$, $R^3$, L, p, and n are as defined herein, ----- is a single or double bond, and the triazole or triazoline is covalently bound (directly or indirectly through a linker) through one (e.g., where the substrate-bound alkenyl or alkynyl group is acyclic) or both (e.g., where the substrate-bound alkenyl or alkynyl group is part of a ring) triazole/triazoline ring carbon atoms to the substrate.

Some example substrate-bound monomer units are therefore represented by Formula (Vb), (Vc), (Vd), or (Ve):

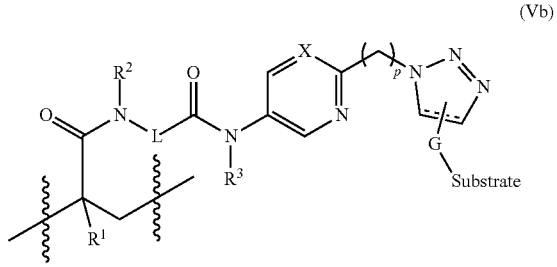
(Vb)

-continued

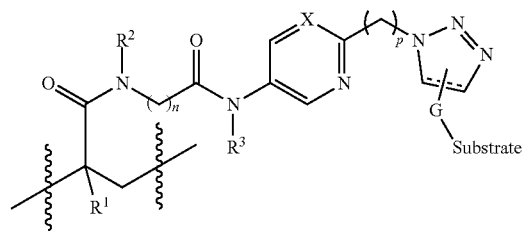
(Vc)

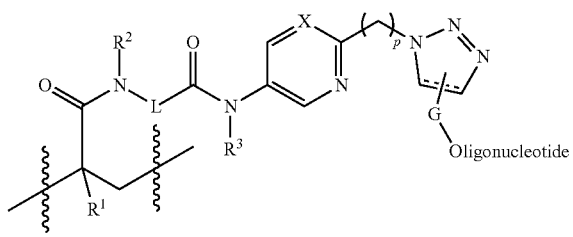
(VIb)

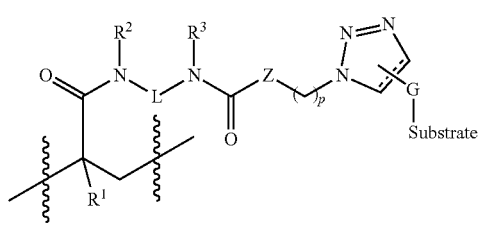
(Vd)

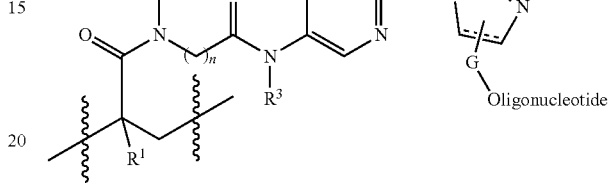
(VIc)

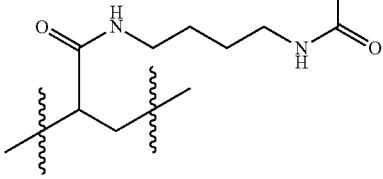
(Ve)

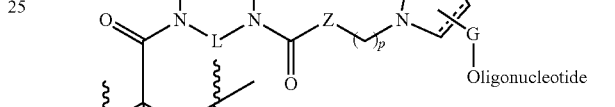
(VId)

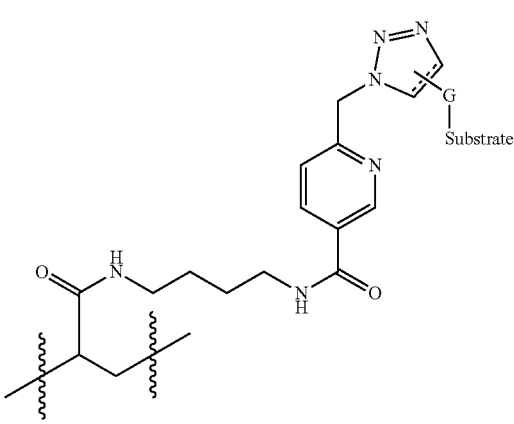

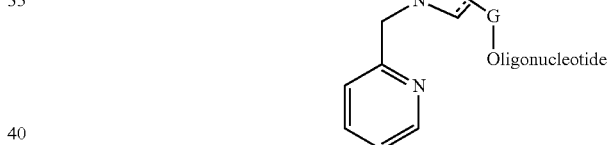
(VIe)

wherein G is a linker between the triazole/triazoline ring and the substrate.

The copolymers described herein may also be covalently bound to oligonucleotides. In some examples, oligonucleotides are covalently bonded to the copolymer through reaction of the azido group of the recurring monomer unit of Formula (II), (IIa), (IIb), (IIc), (IId), or (IIe) and an alkene- or alkyne-functionalized oligonucleotide. Because not all azido groups in a copolymer necessarily would react, some examples provided by the present application are directed to an oligonucleotide-bound copolymer comprising a recurring monomer unit of Formula (II), (IIa), (IIb), (IIc), (IId), or (IIe). In some examples, the oligonucleotide-bound copolymer further comprises a recurring monomer unit that is covalently bound to an oligonucleotide. In some examples, the oligonucleotide-bound copolymer comprises a recurring monomer unit of Formula (IV), (IVa), (IVb), (IVc), (IVd), or (IVe), wherein $R^1$, $R^2$, $R^3$, L, p, and n are as defined herein, ----- is a single or double bond, and the copolymer is covalently bound (directly or indirectly through a linker) through one or both triazole/triazoline ring carbon atoms to the oligonucleotide. Examples of such structures are oligonucleotide-bound recurring monomer units of Formula (VIb), (VIc), (VId), or (VIe):

where the variables are all as defined herein.

Some examples provided in the present application are further directed to copolymers that are covalently bound to both a substrate and to oligonucleotides. Thus, in some examples is a copolymer comprising recurring monomer units of one or more of Formula (V), (Va), (Vb), Formula (VIc), (VId), and (VIe).

Some examples provided by the present application are directed to methods of making a compound of Formula (Ik), methods of making a copolymer comprising a recurring monomer unit of Formula (IIb), and methods of making a copolymer comprising a recurring monomer unit of Formula (IIb) and a recurring monomer unit of Formula (III).

Some examples provided in the present application are directed to a method of immobilizing a copolymer as described herein to a substrate comprising reacting azido groups of a copolymer comprising a recurring monomer unit of Formula (IIb) with a plurality of alkenyl- or alkynyl-containing functional groups on a surface of the substrate to form covalent bonds between the copolymer and the surface.

Some examples provided in the present application are directed to a method of grafting a plurality of oligonucleotides to a copolymer as described herein, comprising reacting azido groups of the copolymer with the oligonucleotides. In some examples, the oligonucleotides comprise alkenyl or alkynyl groups. In some examples, the oligonucleotides comprise alkynyl groups. In some examples, the oligonucleotides are reacted with the copolymer prior to immobilization of the copolymer on a surface of a substrate. In some examples, the oligonucleotides are reacted with the copolymer after immobilization of the copolymer on a surface of a substrate.

It is to be understood that any respective features/examples of each of the aspects of the disclosure as described herein may be implemented together in any appropriate combination, and that any features/examples from any one or more of these aspects may be implemented together with any of the features of the other aspect(s) as described herein in any appropriate combination.

DETAILED DESCRIPTION

Unless defined otherwise, all technical and scientific terms used herein have the same meaning as is commonly understood by one of ordinary skill in the art. The use of the term "including" as well as other forms, such as "include," "includes," and "included," is not limiting. The use of the term "having" as well as other forms, such as "have," "has," and "had," is not limiting. As used in this specification, whether in a transitional phrase or in the body of the claim, the terms "comprise(s)" and "comprising" are to be interpreted as having an open-ended meaning. That is, the above terms are to be interpreted synonymously with the phrases "having at least" or "including at least." For example, when used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

The terms "substantially", "approximately", and "about" used throughout this Specification are used to describe and account for small fluctuations, such as due to variations in processing. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

As used herein, the term "array" refers to a population of different probe molecules that are attached to one or more substrates such that the different probe molecules can be differentiated from each other according to relative location. An array can include different probe molecules that are each located at a different addressable location on a substrate. Alternatively or additionally, an array can include separate substrates each bearing a different probe molecule, wherein the different probe molecules can be identified according to the locations of the substrates on a surface to which the substrates are attached or according to the locations of the substrates in a liquid.

As used herein, the term "covalently attached" or "covalently bonded" refers to the forming of a chemical bonding that is characterized by the sharing of pairs of electrons between atoms. For example, a covalently attached polymer coating refers to a polymer coating that forms chemical bonds with a functionalized surface of a substrate, as compared to attachment to the surface via other means, for example, adhesion or electrostatic interaction. It will be appreciated that polymers that are attached covalently to a surface can also be bonded via means in addition to covalent attachment.

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means fluorine, chlorine, bromine, or iodine, with fluorine and chlorine being examples.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_{1-4}$ alkyl" or similar designations. By way of example only, "$C_{1-4}$ alkyl" or "$C_{1-4}$alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-prop en-1-yl, 2-methyl-prop en-1-yl, 1-ethyl-ethen-1-yl, 2-methyl-prop en-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

Groups that comprise an alkenyl group include optionally substituted alkenyl, cycloalkenyl, and heterocycloalkenyl groups.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2-4}$ alkynyl" or similar designations. By way of example only, "$C_{2-4}$ alkynyl" or "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

Groups that comprise an alkynyl group include optionally substituted alkynyl, cycloalkynyl, and heterocycloalkynyl groups.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some examples, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "heterocycle" refers to a cyclic compound which includes atoms of carbon along with another atom (heteroatom), for example nitrogen, oxygen or sulfur. Heterocycles may be aromatic (heteroaryl) or aliphatic. An aliphatic heterocycle may be completely saturated or may contain one or more or two or more double bonds, for example the heterocycle may be a heterocycloalkyl. The heterocycle may include a single heterocyclic ring or multiple heterocyclic rings that are fused.

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some examples, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

As used herein, "cycloalkyl" means a fully saturated carbocyclyl ring or ring system. Examples include cyclopropyl, cyclobutyl, cyclopentyl, and cyclohexyl.

As used herein, "cycloalkenyl" or "cycloalkene" means a carbocyclyl ring or ring system having at least one double bond, wherein no ring in the ring system is aromatic. An example is cyclohexenyl or cyclohexene. Another example is norbornene or norbornenyl.

As used herein, "heterocycloalkenyl" or "heterocycloalkene" means a carbocyclyl ring or ring system with at least one heteroatom in ring backbone, having at least one double bond, wherein no ring in the ring system is aromatic. In some examples, heterocycloalkenyl or heterocycloalkene ring or ring system is 3-membered, 4-membered, 5-membered, 6-membered, 7-membered, 8-membered, 9-membered, or 10-membered.

As used herein, "cycloalkynyl" or "cycloalkyne" means a carbocyclyl ring or ring system having at least one triple bond, wherein no ring in the ring system is aromatic. An example is cyclooctyne. Another example is bicyclononyne.

As used herein, "heterocycloalkynyl" or "heterocycloalkyne" means a carbocyclyl ring or ring system with at least one heteroatom in ring backbone, having at least one triple bond, wherein no ring in the ring system is aromatic. In some examples, heterocycloalkynyl or heterocycloalkyne ring or ring system is 3-membered, 4-membered, 5-membered, 6-membered, 7-membered, 8-membered, 9-membered, or 10-membered.

As used herein, "heterocycloalkyl" means a non-aromatic cyclic ring or ring system containing at least one heteroatom in the ring backbone. Heterocycloalkyls may be joined together in a fused, bridged or spiro-connected fashion. Heterocycloalkyls may have any degree of saturation provided that at least one heterocyclic ring in the ring system is not aromatic. The heterocycloalkyl group may have 3 to 20 ring members (i.e., the number of atoms making up the ring backbone, including carbon atoms and heteroatoms), although the present definition also covers the occurrence of the term "heterocycloalkyl" where no numerical range is designated. The heterocycloalkyl group may also be a medium size heterocycloalkyl having 3 to 10 ring members. The heterocycloalkyl group could also be a heterocycloalkyl having 3 to 6 ring members. The heterocycloalkyl group may be designated as "3-6 membered heterocycloalkyl" or similar designations. In some six membered monocyclic heterocycloalkyls, the heteroatom(s) are selected from one up to three of O, N or S, and in some five membered monocyclic heterocycloalkyls, the heteroatom(s) are selected from one or two heteroatoms selected from 0, N, or S. Examples of heterocycloalkyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

The term "azido" as used herein refers to a —$N_3$ group.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., —$CF_3$), halo($C_1$-$C_6$)alkoxy (e.g., —$OCF_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —$CH_2$—, —$CH_2CH_2$—, —$CH_2CH(CH_3)CH_2$—, and the like. Other radical naming conventions clearly indicate that the radical is a di-radical such as "alkylene" or "alkenylene."

Wherever a substituent is depicted as a di-radical (i.e., has two points of attachment to the rest of the molecule), it is to be understood that the substituent can be attached in any directional configuration unless otherwise indicated. Thus, for example, a substituent depicted as —AE— or

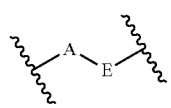

includes the substituent being oriented such that the A is attached at the leftmost attachment point of the molecule as well as the case in which A is attached at the rightmost attachment point of the molecule.

Where the compounds disclosed herein have at least one stereocenter, they may exist as individual enantiomers or diastereomers, or as mixtures of such isomers, including racemates. Separation of the individual isomers or selective synthesis of the individual isomers is accomplished by application of various methods which are well known to practitioners in the art. Where compounds disclosed herein are understood to exist in tautomeric forms, all tautomeric forms are included in the scope of the structures depicted. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

As used herein, a "nucleotide" includes a nitrogen containing heterocyclic base, a sugar, and one or more phosphate groups. They can be monomeric units (whether precursors or linked monomers) of a nucleic acid sequence. In RNA, the sugar is a ribose, and in DNA a deoxyribose, i.e. a sugar lacking a hydroxyl group that is present at the 2' position in ribose. The nitrogen containing heterocyclic base can be purine or pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine.

As used herein, the term "polynucleotide" or "oligonucleotide" refers to nucleic acids in general, including DNA (e.g., genomic DNA or cDNA), RNA (e.g., mRNA), synthetic oligonucleotides, and synthetic nucleic acid analogs such as protected nucleic acids, locked nucleic acids, or bridged nucleic acids. Polynucleotides may include natural or non-natural bases, or combinations thereof and natural or non-natural backbone linkages, e.g. phosphorothioates, PNA or 2'-O-methyl-RNA, or combinations thereof.

As used herein, the term "primer" is defined as a nucleic acid having a single strand with a free 3' OH group. A primer can also have a modification at the 5' terminus to allow a coupling reaction or to couple the primer to another moiety. The primer length can be any number of bases long and can include a variety of non-natural nucleotides. As used herein, "BCN primer" or "BCN modified primer" refers to a primer comprising covalently attached bicyclo[6.1.0] non-4-yne at the 5' terminus. In some examples, a primer is appended with a terminal alkynyl group at the 5' terminus.

In some examples, the primers used on the substrate surface are P5 and P7 primers as used in commercial flow cells sold by Illumina, Inc. for sequencing. The primer sequences are described in U.S. Pat. Pub. No. 2011/0059865 A1, the entire contents of which are incorporated herein by reference. The P5 and P7 primer sequences may comprise the following:

Paired End Set:
P5: paired end 5'→3'

AATGATACGGCGACCACCGAGAUCTACAC

P7: paired end 5'→3'

CAAGCAGAAGACGGCATACGAG*AT

Single Read Set:
P5: single read: 5'→3'

AATGATACGGCGACCACCGA

P7: single read 5'→3'

CAAGCAGAAGACGGCATACGA where G* is 8-oxoguanine.

In some examples, the attached oligonucleotides (such as primers or P5 or P7 primers) comprise a linker or spacer at the 5' end. Such linker or spacer may be included in order to permit chemical or enzymatic cleavage, or to confer some other desirable property, for example to enable covalent attachment to a polymer or a solid support, or to act as spacers to position the site of cleavage an optimal distance from the solid support. In certain cases, 10 spacer nucleotides may be positioned between the point of attachment of the P5 or P7 primers to a polymer or a solid support. In some examples, polyT spacers are used, although other nucleotides and combinations thereof can also be used. In one example, the spacer is a 6T to 10T spacer. In some examples, the linkers include cleavable nucleotides comprising a chemically cleavable functional group such as a vicinal diol or allyl T.

As used herein, the term "silane" refers to an organic or inorganic compound containing one or more silicon atoms. A non-limiting example of an inorganic silane compound is $SiH_4$, or halogenated $SiH_4$ where hydrogen is replaced by one or more halogen atoms. A non-limiting example of an organic silane compound is $X-R^C-Si(OR^D)_3$, wherein X is a non-hydrolyzable organic group, such as amino, vinyl, epoxy, methacrylate, sulfur, alkyl, alkenyl, or alkynyl; $R^C$ is a spacer, for example $-(CH_2)_n-$, wherein n is 0 to 1000; each $R^D$ is independently selected from hydrogen, optionally substituted alkyl, optionally substituted alkenyl, optionally substituted alkynyl, optionally substituted carbocyclyl, optionally substituted aryl, optionally substituted 5-membered heteroaryl, and optionally substituted 5-10 membered heterocyclyl, as defined herein. In some examples, the silanes may be cross-linked such that the oxygen atom of an $-OR^D$ group of $X-R^C-Si(OR^D)_3$, is attached to the silicon atom of an adjacent organic silane compound, $X-R^C-Si(OR^D)_3$. Furthermore, the silane compounds may be attached to a substrate surface by covalent binding of the $X-R^C-Si(OR^D)_3$ moieties to oxygen atoms on the surface. Thus, in some examples, the silanes described comprise the following structure:

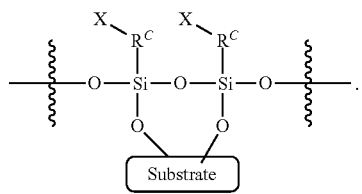

As used herein, the term "silane" can comprise mixtures of different silane compounds. In some examples, X is a norbornenyl group. In some examples, X is a bicyclononynyl group. In some examples, X is an alkene- or alkyne-containing group. In some examples, X is alkene or alkyne. In some examples, the R c linker is a $C_{2-6}$ alkylene group.

As used herein, the term "substrate" refers to a material used as a support for the copolymers described herein. In array methods, beads are coated with polymers that likewise are functionalized to capture target oligonucleotides. Polymer materials for sequencing have been described in U.S. Pat. Publ. Nos. 2014/0079923 and 2016/0122816, both of which are incorporated by reference in their entirety. In examples described herein, the substrate material may comprise glass, silica, plastic, quartz, metal, metal oxide, organo-silicate (e.g., polyhedral organic silsesquioxanes (POSS)), polyacrylates, tantalum oxide, complementary metal oxide semiconductor (CMOS), or combinations thereof. An example of POSS can be that described in Kehagias et al., Microelectronic Engineering 86 (2009), pp. 776-778, which is incorporated by reference in its entirety.

In some examples, substrates used in the present application include silica-based substrates, such as glass, fused silica and other silica-containing materials. In some examples, silica-based substrates can be silicon, silicon dioxide, silicon nitride, silicone hydrides. In some examples, substrates used in the present application include plastic materials or components such as polyethylene, polystyrene, poly(vinyl chloride), polypropylene, nylons, polyesters, polycarbonates, and poly(methyl methacrylate). Example plastics material include poly(methyl methacrylate), polystyrene, and cyclic olefin polymer substrates. In some examples, the substrate is or includes a silica-based material or plastic material or a combination thereof. In particular examples, the substrate has at least one surface comprising glass or a silicon-based polymer. In some examples, the substrate comprises glass. In some examples, the substrates can be, or can contain or include, a metal. In some such examples, the metal is gold. In some examples, the substrate has at least one surface comprising a metal oxide. In one example, the surface comprises a tantalum oxide or tin oxide. Acrylamides, enones, or acrylates may also be utilized as a substrate material or component. Other substrate materials can include, but are not limited to gallium arsenide, indium phosphide, aluminum, ceramics, polyimide, quartz, resins, polymers and copolymers. In some examples, the substrate and/or the substrate surface can be, or include, quartz. In some other examples, the substrate and/or the substrate surface can be, or include, semiconductor, such as GaAs or ITO. The foregoing lists are intended to be illustrative of, but not limiting to the present application. Substrates can comprise a single material or a plurality of different materials. Substrates can be composites or laminates. In some examples, the substrate comprises an organo-silicate material.

Substrates can be flat, round, spherical, rod-shaped, or any other suitable shape. Substrates may be rigid or flexible. In some examples, a substrate is a bead or a flow cell.

Substrates can be non-patterned, textured, or patterned on one or more surfaces of the substrate. In some examples, the substrate is patterned. Such patterns may comprise posts, pads, wells, ridges, channels, or other three-dimensional concave or convex structures. Patterns may be regular or irregular across the surface of the substrate. Patterns can be formed, for example, by nanoimprint lithography or by use of metal pads that form features on non-metallic surfaces, for example.

In some examples, a surface of the substrate comprises both copolymer-coated regions and inert regions. In some examples, the surface of the substrate can comprise both functionalized silane-coated regions and inert regions. For examples that use a patterned substrate, a copolymer or silane can be selectively attached to the pattern features (e.g., can be attached to metal pads or gel can be attached to the interior of wells) or alternatively the copolymer or silane can be uniformly attached across both the pattern features and the interstitial regions and then optionally removed from interstitial regions.

In some examples, a substrate described herein forms at least part of a flow cell or is located in a flow cell. In some such examples, the flow cells further comprise oligonucleotides attached to the surface of the substrate via the copolymer coating. In such examples, the surface of the flow cell body to which the oligonucleotides are attached is considered the substrate. In other examples, a separate substrate having a copolymer-coated surface (e.g., a bead) is inserted into the body of the flow cell. In preferred examples, the flow cell is a flow chamber that is divided into a plurality of lanes or a plurality of sectors, wherein one or more of the plurality of lanes or plurality of sectors comprises a surface that is coated with a copolymer coating described herein. Example flow cells and substrates for manufacture of flow cells that can be used in method or composition set forth herein include, but are not limited to, those commercially available from Illumina, Inc. (San Diego, CA).

As used herein, the term "structure" refers to a compound, for example a copolymer, that is bonded to a substrate. The copolymer may for example be covalently bonded to the substrate, for example via an azido group.

As used herein, the term "polymer" refers to a molecule composed of many repeated subunits or recurring units. Non-limiting examples of polymer structures include linear, branched, or hyper-branched polymers. Non-limiting examples of linear polymers comprising block copolymers or random copolymers. Non-limiting examples of branched polymers include star polymers, star-shaped or star-block polymers comprising both hydrophobic and hydrophilic segments, H-shaped polymers comprising both hydrophobic and hydrophilic segments, dumbbell shaped polymers, comb polymers, brush polymers, dendronized polymers, ladders, and dendrimers. Polymers may be cross-linked, or lightly cross-linked. Polymers as described herein may be linear, branched, hyper-branched or dendritic. The polymers described herein can also be in the form of polymer nanoparticles. Other examples of polymer architectures include, but not limited to ring block polymers and coil-cycle-coil polymers. Polymers with more than one type of recurring unit can be arranged as block copolymers, random copolymers, or alternating copolymers, or mixtures thereof. The final copolymer structure can be in different architectures, including, for example, random copolymer, block copolymer, comb-shaped polymer or star-shaped polymer architectures. Different classes of polymer backbones include, but are not limited to, polyacrylamides, polyacrylates, polyurethanes, polysiloxanes, silicones, polyacroleins, polyphosphazenes, polyisocyanates, poly-ols, polysaccharides, and combinations thereof. In some examples, the polymer comprises polyacrylamide backbone. In some other examples, the polymer comprises polyacrylate backbone. In still some other examples, the polymer comprises polyurethane backbone. In still some other examples, the polymer comprises polyphosphazene backbone. In still some other examples, the polymer comprises a dendrimer backbone.

As used herein, the prefixes "photo" or "photo-" mean relating to light or electromagnetic radiation. The term can encompass all or part of the electromagnetic spectrum including, but not limited to, one or more of the ranges commonly known as the radio, microwave, infrared, visible, ultraviolet, X-ray or gamma ray parts of the spectrum. The part of the spectrum can be one that is blocked by a metal region of a surface such as those metals set forth herein. Alternatively or additionally, the part of the spectrum can be one that passes through an interstitial region of a surface such as a region made of glass, plastic, silica, or other material set forth herein. In particular examples, radiation can be used that is capable of passing through a metal. Alternatively or additionally, radiation can be used that is masked by glass, plastic, silica, or other material set forth herein.

As used herein, the term "YES method" refers to the chemical vapor deposition tool provided by Yield Engineering Systems ("YES") with chemical vapor deposition process developed by Illumina, Inc. It includes three different vapor deposition systems. The automated YES-VertaCoat silane vapor system is designed for volume production with a flexible wafer handling module that can accommodate 200 or 300 mm wafers. The manual load YES-1224P Silane Vapor System is designed for versatile volume production with its configurable large capacity chambers. Yes-LabKote is a low-cost, tabletop version that is ideal for feasibility studies and for R&D.

In an aspect, there is provided a compound according to formula (I).

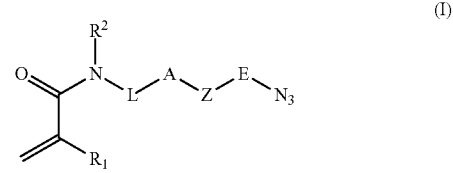

wherein
$R^1$ is H or $C_{1-4}$ alkyl;
$R^2$ is H or $C_{1-4}$ alkyl;
L is a linker comprising a linear chain comprising 2 to 20 atoms selected from the group consisting of carbon, oxygen, and nitrogen and optional substituents on the carbon and any nitrogen atoms in the chain;
E is a linear chain comprising 1 to 4 atoms selected from the group consisting of carbon, oxygen and nitrogen, and optional substituents on the carbon and any nitrogen atoms in the chain;

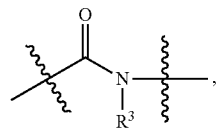

A is an N substituted amide having formula wherein $R^3$ is H or $C_{1-4}$ alkyl; and
Z is a nitrogen containing heterocycle.

Compounds according to formula (I) can function as polymerisable monomers. For example, the presence of the acryloyl group can provide a polymerisable moiety, optionally allowing a plurality of such compounds (monomers) to be polymerized with one another and optionally with one or more other types of compounds (monomers). Additionally, or alternatively, the azido group present in the compounds of formula (I) optionally can undergo cycloaddition reactions with one or more suitable compounds, such as one or more suitable alkene or alkyne containing compounds. Illustratively, it has been found that the presence of a nitrogen containing heterocyclic group close to the azido group can lead to an increased rate of copper mediated cycloaddition reactions, for example an increase of 20-38 times as compared to compounds which do not include a nitrogen containing heterocyclic group that is close to the azido group. This means that less copper catalyst is involved to catalyse the cycloaddition reaction. Without wishing to be bound by any theory, it is believed that the nitrogen within the nitrogen containing heterocycle may co-ordinate with (e.g., chelate) the copper catalyst, such that the copper center of the copper catalyst can be bound at a location sufficiently close to the azido group as to more readily catalyse the cycloaddition reaction between the azido group and an alkene or alkyne containing compound, thus increasing the reaction rate and decreasing copper catalyst consumption. In some examples, the nitrogen within the nitrogen containing heterocycle is located at a distance of approximately 5 nm or less from the azido group so as to facilitate co-ordination with the copper centre of the copper catalyst, e.g., a distance of approximately 1 Angstrom to 5 nm, or a distance of approximately 2 Angstroms to 2 nm, or a distance of approximately 5 Angstroms to 1 nm. The monomer compounds disclosed herein optionally can form polymers or copolymers, which optionally may be used to coat a substrate to thereby functionalise the substrate. For example, the polymer or copolymer coated substrate may react with alkene or alkyne functionalised biological molecules.

E may for example be optionally substituted $C_{1-4}$ alkylene, each carbon optionally substituted with one or more substituents selected from, for example, —$C_{1-4}$ alkyl, —OH, —$OC_{1-4}$ alkyl, or =O. E may be for example an unsubstituted $C_{1-4}$ alkylene, for example $CH_2$, $(CH_2)_2$, $(CH_2)_3$ or $(CH_2)_4$.

Optionally, E may comprise an ether, an ester or an amide. For example, E may comprise —$CH_2CH_2OCH_2$—, —COC-$NHCH_2$— or —$CH_2COOCH_2$—.

$R^1$ may for example be H or a linear or branched chain alkyl group having between 1 and 4 carbon atoms. For example, $R^1$ may be H or methyl, ethyl, propyl, isopropyl, butyl, isobutyl, sec-butyl, or tert-butyl. Illustratively, $R^1$ may be H or methyl.

$R^2$ may for example be H or a linear or branched chain alkyl group having between 1 and 4 carbon atoms, for example methyl, ethyl, propyl, isopropyl, butyl, isobutyl, sec-butyl, or tut-butyl. For example, $R^2$ may be H or methyl.

$R^3$ may for example be H or a linear or branched chain alkyl group having between 1 and 4 carbon atoms, for example methyl, ethyl, propyl, isopropyl, butyl, isobutyl, sec-butyl, or tut-butyl. For example, $R^3$ may be H or methyl.

In some examples, L may be a linker including a linear chain that is a —$C_{2-20}$ alkylene- or a 3 to 20 atom linear heteroalkylene, each optionally substituted with one or more substituents selected from the group consisting of —$C_{1-4}$ alkyl, —OH, —$OC_{1-4}$ alkyl, or =O. L may be a linker with a linear chain that is a —$C_{2-6}$ alkylene-, optionally substituted with one or more —$C_{1-4}$ alkyl, —OH, —$OC_{1-4}$ alkyl, or =O substituents. L may be unsubstituted —$C_{2-6}$ alkylene- (also drawn as —$(CH_2)_{2-6}$—), for example L may be unsubstituted —$C_{3-4}$ alkylene-, for example —$(CH_2)_3$— or —$(CH_2)_4$—. L may be a linker including a linear chain that is a 3 to 20 atom linear heteroalkylene, optionally substituted with one or more substituents selected from the group consisting of —$C_{1-4}$ alkyl, —OH, —$OC_{1-4}$ alkyl, or =O. Illustratively, L may comprise one or more ethylene glycol units. L may be —$CH_2CH_2(OCH_2CH_2)_x$—$OCH_2CH_2$—, in which x is 0 to 10. In one nonlimiting example, x is 1, 2, 3, 4, 5, or 6. L may comprise one or more amide groups. For example L may be —$C_{2-6}$ alkyl-NHC(O)—$C_{2-6}$ alkyl-, or L may be —$(CH_2)_2$—NHC(O)—$(CH_2)_2$— or —$(CH_2)_3$—NHC(O)—$(CH_2)_2$—. L may comprise one or more natural or unnatural amino acids, for example L may comprises one or more natural amino acids, for example L may comprise one or more amino acids selected from the group consisting of glycine, alanine, valine, isoleucine, leucine, lysine, serine, threonine, cysteine, asparagine, or glutamine. In some examples, L may comprise 1, 2, or 3 amino acid units.

The N substituted amide A may be bonded to L and Z in two possible configurations, for example the carbonyl carbon of A may be bonded to L and the amide nitrogen of A may be bonded to Z. Alternatively, the carbonyl carbon of A may be bonded to Z and the amide nitrogen of A may be bonded to L. Examples of these two configurations are set out as formulae (Ic) and (Id) below.

Z may comprise a nitrogen containing heterocycle having from 5 to 10 ring members, e.g., a 5 to 10 membered heterocyclic ring, wherein the ring members are the atoms that form the back bone of the heterocyclic ring. Z may comprise a single cyclic structure or a fused structure comprising two or more ring systems. In the case of single cyclic structure, Z may comprise 5 or 6 ring members, e.g. Z may be a 5 or 6 membered heterocyclic ring. In the case of fused structure, Z may comprise 9 or 10 ring members. The nitrogen containing heterocycle may comprise more than one heteroatom, for example one or more additional nitrogen heteroatoms, or one or more oxygen heteroatoms, or one or more sulphur heteroatoms, or any suitable combination of such heteroatoms. The nitrogen containing heterocycle may be aromatic, for example pyridinyl, pyrimidinyl, pyrrolyl, pyrrazolyl, imidazolyl, indolyl, quinolinyl, quinazolinyl. The nitrogen containing heterocycle may be aliphatic, for example a cycloalkyl. The aliphatic nitrogen containing heterocycle may be saturated or may include one or more double bonds while not being aromatic. In one example, the aliphatic nitrogen containing heterocycle may be pyrrolidinyl.

In the case of Z being a 6 membered heterocyclic ring, the compound of formula (I) optionally can be configured such that A is bonded at position 2 of the 6 membered ring (the N constituting position 1) and the alkyl azido group is bonded at position 5 of the six membered ring. Such a configuration may be considered to provide a 1,4 substitution pattern with respect to the 6 membered heterocyclic ring.

In some options, the compound of formula (I) may be of formula (Ia):

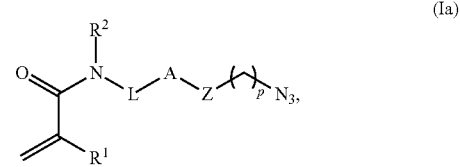
(Ia)

in which $R^2$, L, A and Z are as defined above for formula (I) and p is 1, 2, 3 or 4.

In some options, the compound of formula (Ia) may be of formula (Ib)

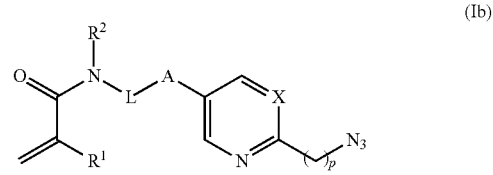
(Ib)

wherein $R^1$, $R^2$, L, A and p are as defined above for formula (I) and (Ia), and X is CH or N.

The compound of formula (Ia) optionally may be a compound of formula (Ic)

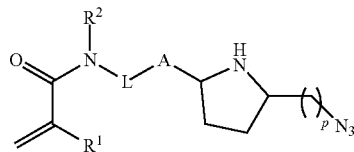
(Ic)

in which R², L, A and p are as defined above for formula (I) and (Ia).

As noted above, the compound of formula (Ia) optionally may be a compound of formula (Id) or (Ie)

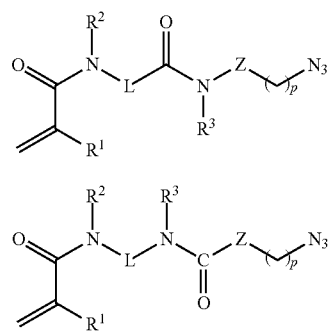
(Id)

(Ie)

in which R¹, R², L, A and p are as defined above for formula (I) and (Ia). That is, A can have any suitable configuration.

In some examples, the compound of formula (Ib) and (Id) may be a compound of formula (Ik)

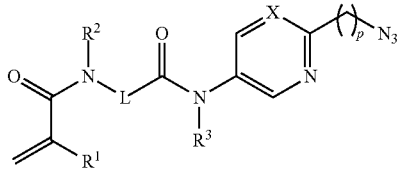
(Ik)

wherein R¹, R², R³, X and p are as defined above for formula (I), formula (Ia) and formula (Ib).

The compound for formula (Ik) optionally may be a compound of formula (Im)

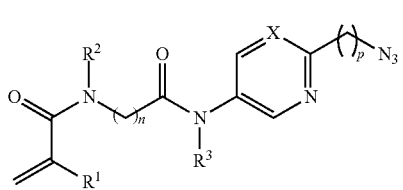
(Im)

wherein R¹, R², R³, X and p are as defined above for formula (I), formula (Ia) and formula (Ib), and n is an integer from 2 to 20. For example, n may be an integer between 1 and 10, for example between 1 and 6, for example 2, 3, 4, 5, or 6. For example n may be 3 or 4.

In one specific and nonlimiting example, the compound of formula (I), (Ia), (Ib) and (Ie) may be a compound having the formula (If)

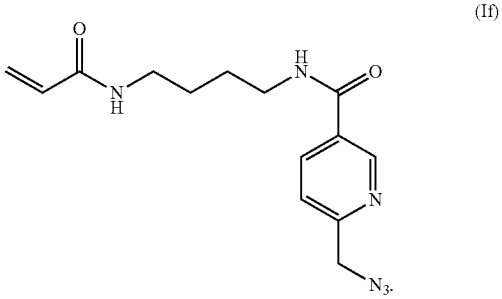 [SMILES: C=CC(=O)NCCCCNC(=O)c1ccc(CN=[N+]=[N-])nc1]
(If)

In another specific and nonlimiting example, the compound of formula (I), (Ia) (Ic) and (Ie) may be a compound having the formula (Ig).

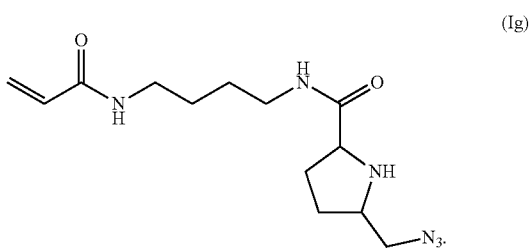 [SMILES: C=CC(=O)NCCCCNC(=O)C1CCC(CN=[N+]=[N-])N1]
(Ig)

In still other nonlimiting examples, the compound of formula (I), (Ia), (Ib) and (Id) may be a compound having the formula (Ih) or (Ij):

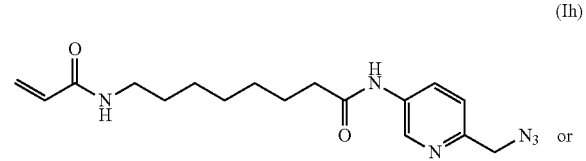
(Ih)

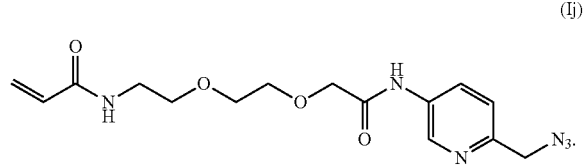
(Ij)

In some aspects, there is provided a copolymer that is formed from reacting a compound as defined by formula (I), (Ia), (Ib), (Ic), (Id), (Ie), (If), (Ig), (Ih), (Ij), (Ik) or (Im) with at least one other recurring monomer unit.

In some aspects, there is provided a copolymer comprising a recurring monomer unit of Formula (II)

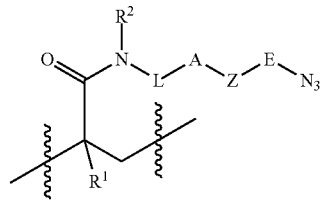
(II)

wherein R¹ is H or $C_{1-4}$ alkyl;
R² is H or $C_{1-4}$ alkyl;
L is a linker comprising a linear chain comprising 2 to 20 atoms selected from the group consisting of carbon, oxygen, and nitrogen and optional substituents on the carbon and any nitrogen atoms in the chain;
E is a linear chain comprising 1 to 4 atoms selected from the group consisting of carbon, oxygen and nitrogen, and optional substituents on the carbon and any nitrogen atoms in the chain;
A is an N substituted amide having formula

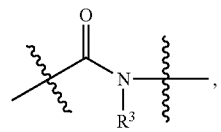

wherein R³ is H or $C_{1-4}$ alkyl; and
Z is a nitrogen containing heterocycle; and
at least one other recurring monomer unit.

It will be appreciated that R², L, A, Z and E may be defined as set out above for formula (I).

It will be appreciated that the recurring monomer unit of formula (II) can be derived from the compound of formula (I). The carbon carbon double bond in the acryloyl group of the compound of formula (I) may polymerise to thereby result in a copolymer comprising a recurring monomer unit of formula (I). It will be appreciated that the recurring monomer unit of formula (II) may be derived from any of the compounds of formula (I), (Ia), (Ib), (Ic), (Id), (Ie), (If), (Ig), (Ih), (Ij), (Ik) or (Im).

Optionally, the at least one other recurring monomer unit may be selected from the group consisting of a polyacrylamide, a polyacrylate, a polyurethane, a polysiloxane, a silicone, a polyacrolein, a polyphosphazene, a polyisocyanate, a poly-ol, and a polysaccharide, and any combinations thereof.

The copolymer may, for example, comprise a recurring monomer unit of formula (IIa):

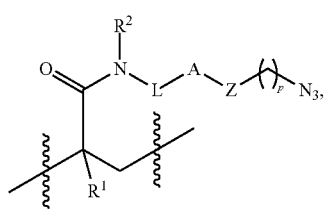
(IIa)

in which R², L, A, Z and p are as defined above for formula (I) and (Ia).

The copolymer may, for example, comprise a recurring monomer unit of formula (IIb), (IIc), (IId), or (IIe):

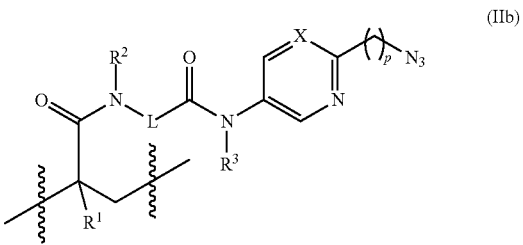
(IIb)

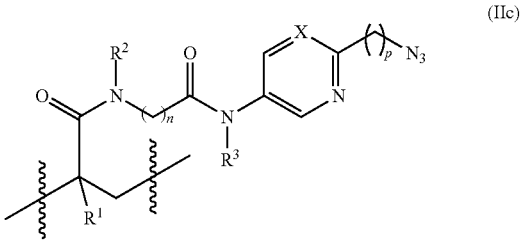
(IIc)

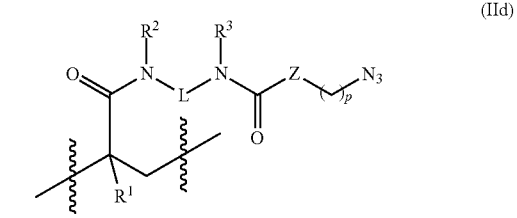
(IId)

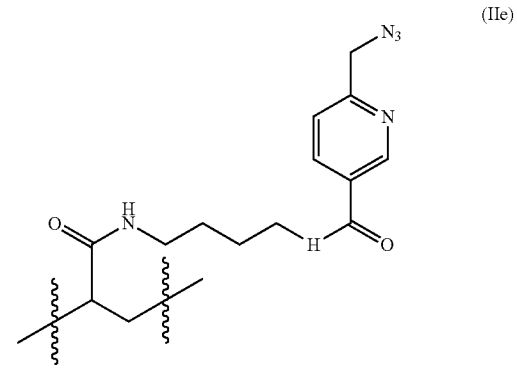
(IIe)

in which R² and X are as defined above for formula (I), (Ia) and (Ib), and n in formula (IIc) is an integer from 2 to 20.

The at least one other recurring monomer unit optionally may be a compound of formula (III)

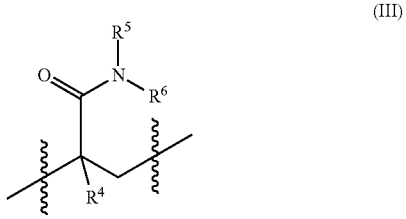
(III)

wherein $R^4$ is H or $C_{1-4}$alkyl;

$R^5$ is H or $C_{1-4}$alkyl; and $R^6$ is H or $C_{1-4}$alkyl.

$R^4$ may for example be H or a linear or branched chain alkyl group having between 1 and 4 carbon atoms. For example, $R^4$ may be H or methyl, ethyl, propyl, isopropyl, butyl, isobutyl, sec-butyl, or tert-butyl, Illustratively, $R^4$ may be H or methyl.

$R^5$ may for example be H or a linear or branched chain alkyl group having between 1 and 4 carbon atoms, for example methyl, ethyl, propyl, isopropyl, butyl, isobutyl, sec-butyl, or tert-butyl. For example, $R^5$ may be H or methyl.

$R^6$ may for example be H or a linear or branched chain alkyl group having between 1 and 4 carbon atoms, for example methyl, ethyl, propyl, isopropyl, butyl, isobutyl, sec-butyl, or tert-butyl. For example, $R^6$ may be H or methyl.

The copolymer may comprise a recurring monomer unit of Formula (II), (IIa), (IIb), (IIc), (IId), or (IIe), a recurring monomer unit of Formula (III), and at least one other recurring monomer unit.

In another aspect, there is provided a substrate-copolymer product formed from the reaction of the copolymer as set out above with reference to formulae (II), (Iia), (IIb), (IIc), (IId), or (IIe) with a substrate, for example a substrate as described herein. The substrate co-polymer product may be formed by reaction of the azido group of the copolymer with an alkenyl or alkynyl-containing group on a surface of the substrate.

Reacting the substrate with the copolymer as set out above can result in a functionalized substrate in which pendent azido groups are configured to react with alkenyl or alkynyl groups found in target molecules, for example biomolecules or functionalized biomolecules. The functionalized substrate may be used for applications such as sequencing or molecular analysis.

In another aspect, there is provided a structure comprising a copolymer covalently bound to the substrate, wherein the substrate-bound copolymer comprises a recurring monomer unit that is covalently bound to the substrate, wherein the recurring, covalently-bound monomer unit is a compound of Formula (IV):

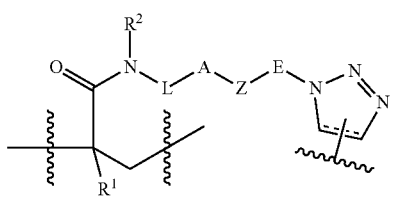

(IV)

wherein $R^1$, $R^2$, L, A, Z, E are defined as set out above for formula (I), is a single or double bond; and the triazole or triazoline is covalently bound, directly or indirectly through a linker, through one or both triazole/triazoline ring carbon atoms to the substrate. It will be appreciated that the recurring covalently bound monomer unit of formula (IV) can be derived from the compound of formula (I). It will be appreciated that the recurring monomer unit of formula (IV) may be derived from any of the compounds of formula (I), (Ia), (Ib), (Ic), (Id), (Ie), (If), (Ig), (Ih), (Ij), (Ik) or (Im).

The recurring, covalently-bound, monomer unit may be a compound of Formula (IVa),

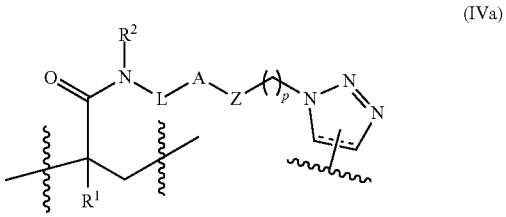

(IVa)

wherein $R^1$, $R^2$, L, A, Z and p are as defined as set out above for formula (I) and (Ia), is a single or double bond; and the triazole or triazoline is covalently bound, directly or indirectly through a linker, through one or both triazole/triazoline ring carbon atoms to the substrate.

The recurring, covalently-bound, monomer unit may be a compound of Formula (IVb), (IVc), (IVd), or (IVe):

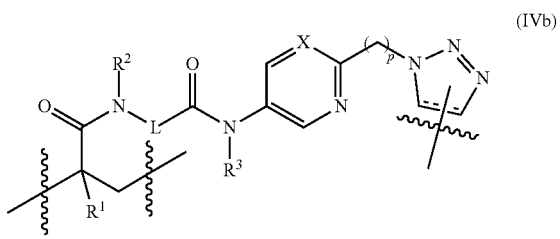

(IVb)

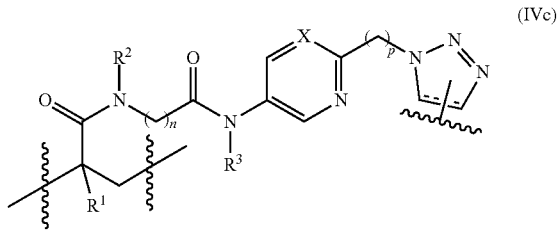

(IVc)

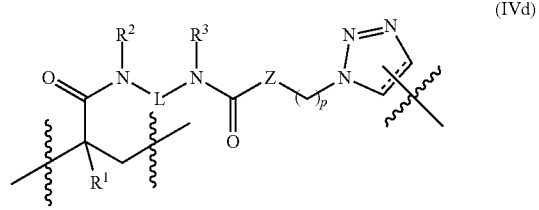

(IVd)

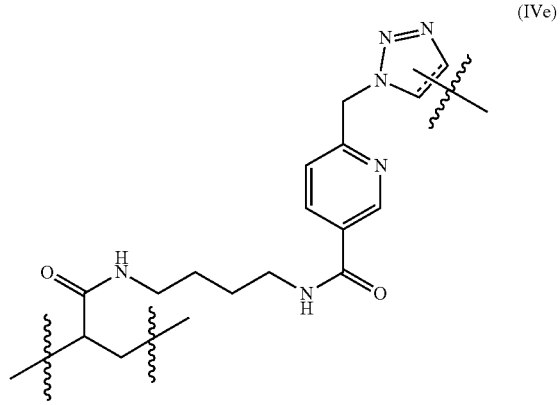

(IVe)

wherein $R^1$, $R^2$, $R^3$, X and p are as defined as set out above for formula (I), (Ia) and (Ib), is a single or double bond; and the triazole or triazoline is covalently bound, directly or indirectly through a linker, through one or both triazole/triazoline ring carbon atoms to the substrate; and n in formula (IVc) is an integer from 2 to 20. For example, n may be an integer between 1 and 10, for example between 1 and 6, for example 2, 3, 4, 5, or 6, for example n may be 3 or 4.

The recurring, covalently-bound, monomer unit may be a compound of Formula (V)

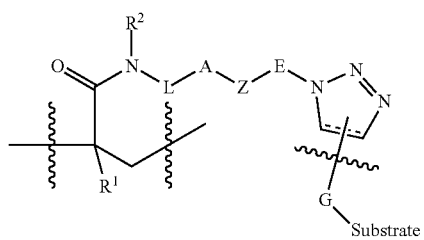
(V)

wherein $R^1$, $R^2$, L, A, Z and E are as defined above for formula (I), and wherein G is a linker between the triazole/triazoline ring and the substrate.

G may, for example, be a silane linker. For example, G may be —X'—$R^C$—Si(O—)$_3$, where X' is the product of a reaction of a group X of a silane linker precursor with an azido group of the copolymer. X may be alkenyl, alkynyl, norbornenyl, or bicyclononynyl. X' may be a single bond, a double bond,

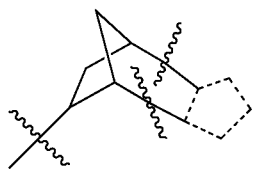

in which the dotted 5-membered ring is the triazoline unit, or

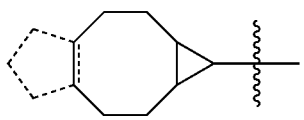

in which the dotted 5-membered ring is the triazoline unit. In some examples, G is -cycloalkyl-CH$_2$CH$_2$—Si(O—)$_3$ in which the cycloalkyl is fused to the triazoline unit. In some examples, G is -cycloalkenyl-CH$_2$CH$_2$—Si(O—)$_3$ in which the cycloalkenyl is fused to and shares the double bond with the triazole unit.

The recurring, covalently-bound monomer unit may be a compound of formula (Va)

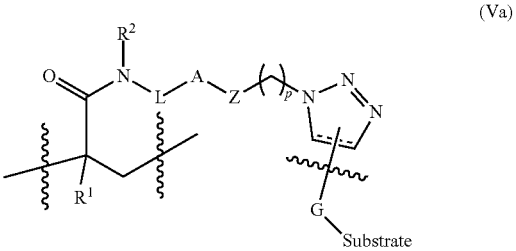
(Va)

wherein $R^1$, $R^2$, L, A Z and p are as defined as set out above for formula (I), and (Ia), and G is as defined above for formula (V).

The recurring, covalently-bound monomer unit may be a compound of formula (Vb), formula (Vc), formula (Vd), or formula (Ve):

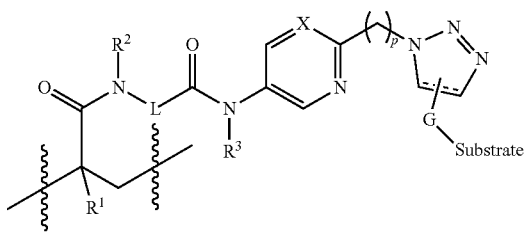
(Vb)

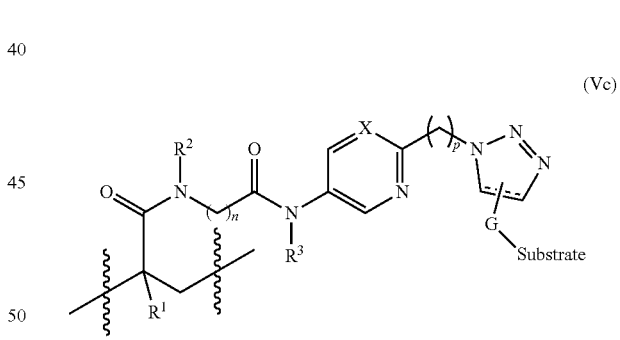
(Vc)

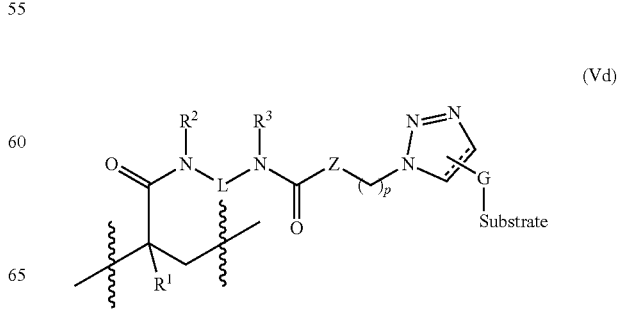
(Vd)

-continued (Ve)

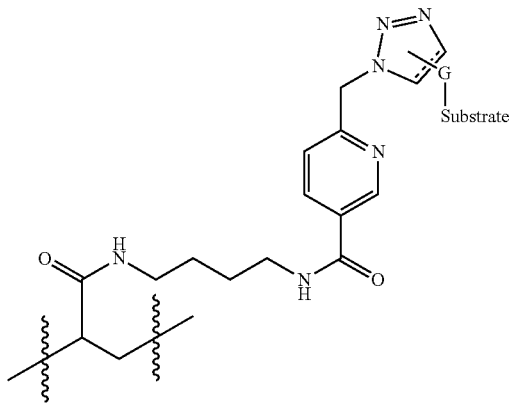

wherein $R^1$, $R^2$, $R^3$, X and p are as defined above for formula (I), formula (Ia) and formula (Ib); G is as defined above for formula (V); and n in formula (Vc) is an integer from 2 to 20. For example, n may be an integer between 1 and 10, for example between 1 and 6, for example 2, 3, 4, 5, or 6, for example n may be 3 or 4.

In an aspect, there is provided a copolymer-oligonucleotide product formed from the reaction between the copolymer as defined by formulae (II), (IIa), (IIb), (IIc), (IId), or (IIe) and one or more oligonucleotides. The copolymer oligonucleotide product may be formed from reaction of the azido group of the copolymer and an alkene- or alkyne-functionalized oligonucleotide.

Illustratively, the oligonucleotide may be or include DNA, RNA, genomic DNA, template DNA fragments, or a primer such as an amplification primer. The amplification primer may be a P5 or P7 sequence for use in sequencing-by-synthesis systems.

In another aspect, there is provided an oligonucleotide bound copolymer comprising a recurring monomer unit of Formula (IV):

(IV)

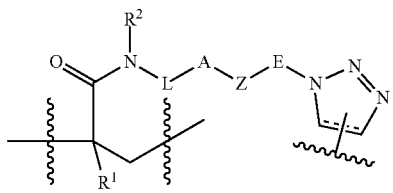

wherein $R^1$, $R^2$, $R^3$, L, A, Z and E are as defined above for formula (I);

----- is a single or double bond; and the copolymer is covalently bound, directly or indirectly through a linker, through one or both triazole/triazoline ring carbon atoms to the oligonucleotide.

It will be appreciated that the recurring monomer unit of formula (IV) can be derived from the compound of formula (I). It will be appreciated that the recurring monomer unit of formula (IV) may be derived from any of the compounds of formula (I), (Ia), (Ib), (Ic), (Id), (Ie), (If), (Ig), (Ih), (Ij), (Ik) or (Im).

For example, the oligonucleotide-bound recurring monomer unit may be of formula (IVa):

(IVa)

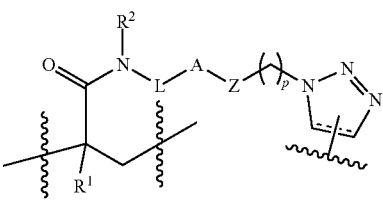

wherein $R^1$, $R^2$, $R^3$, L, A, Z and p are as defined above for formula (I) and formula (Ia);

----- is a single or double bond; and the copolymer is covalently bound, directly or indirectly through a linker, through one or both triazole/triazoline ring carbon atoms to the oligonucleotide.

For example, the oligonucleotide-bound recurring monomer unit may be of formula (IVb), (IVc), (IVd), or (IVe):

(IVb)

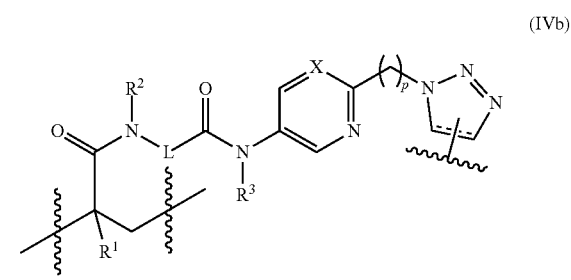

(IVc)

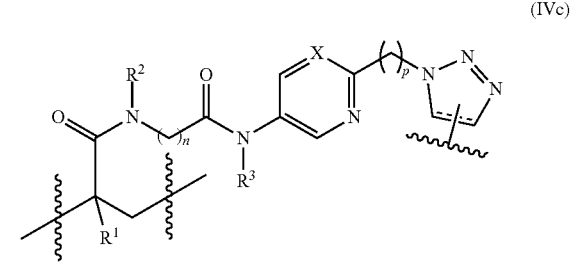

(IVd)

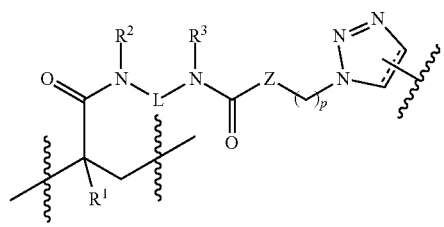

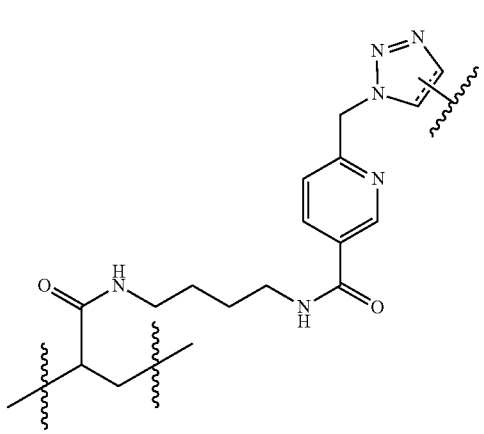

(IVe)

wherein $R^1$, $R^2$, p and X are as defined above for formula (I), (Ia) and (Ib); and n in formula (IVc) is an integer from 2 to 20. For example, n may be an integer between 1 and 10, for example between 1 and 6, for example 2, 3, 4, 5, or 6, for example n may be 3 or 4.

In some examples, the oligonucleotide-bound recurring monomer unit may be of formula (VI):

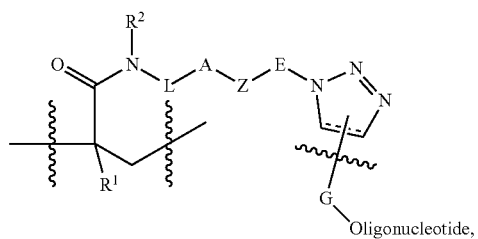

(VI)

in which $R^1$, $R^2$, L, A, Z and E are as defined above for formula (I); ===== is a single or double bond; and G is as defined above for formula (V).

The oligonucleotide-bound recurring monomer unit may be of formula (VIa):

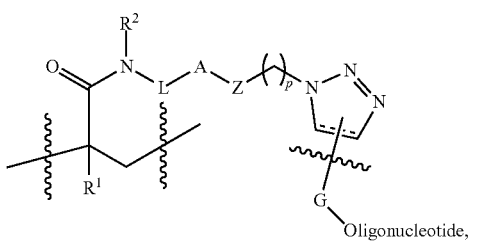

(VIa)

wherein $R^1$, $R^2$, L, A, Z and p are as defined as set out above for formula (I) and (Ia) and G is defined above for formula (V).

In some examples, the oligonucleotide-bound recurring monomer units may optionally be of formula (VIb) or formula (VIc), Formula (VId), or Formula (VIe):

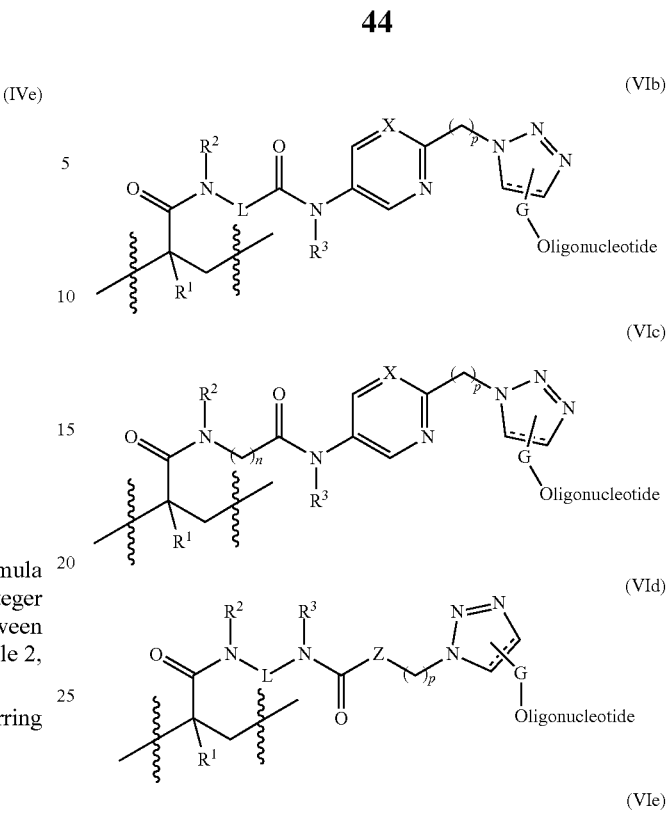

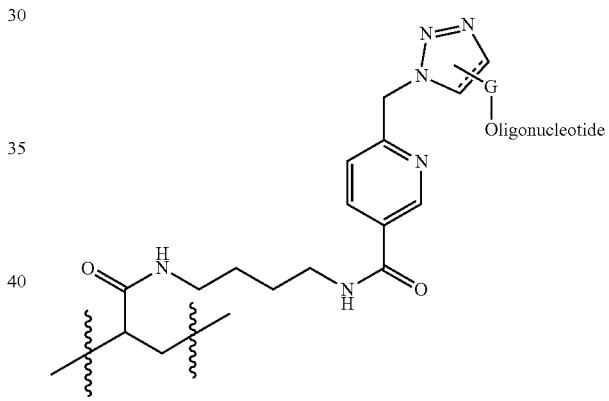

wherein $R^1$, $R^2$, $R^3$, X and p are as defined above for formula (I), formula (Ia) and formula (Ib); G is as defined above for formula (V); and n in formula (VIc) is an integer from 2 to 20. For example, n may be an integer between 1 and 10, for example between 1 and 6, for example 2, 3, 4, 5, or 6, for example n may be 3 or 4.

In another aspect, there is provided a copolymer-substrate-oligonucleotide product formed by reaction of the copolymer as set out above with reference to formula (II), (IIa), (IIb), (IIc), (IId), or (IIe) with a substrate and one or more oligonucleotides. The one or more oligonucleotides may include DNA, RNA, genomic DNA, template DNA fragments, or a primer such as an amplification primer. The amplification primer may be a P5 or P7 sequence for use in sequencing-by-synthesis systems.

In another aspect, there is provided a method of immobilizing a copolymer as set out above with reference to formulae (II), (IIa), (IIb), (IIc), (IId), or (IIe) to a substrate comprising reacting azido groups of the copolymer with a plurality of alkenyl- or alkynyl-containing functional groups on a surface of the substrate to form covalent bonds between the copolymer and the surface of the substrate. The alkene- or alkyne-containing functional group may be, for example, alkenyl, alkynyl, cycloalkynyl, or cycloalkenyl. In some specific, nonlimiting examples, the alkene- or alkyne-containing group is norbornenyl. In some specific, nonlimiting examples, the alkene- or alkyne-containing group is a silane. In some specific, nonlimiting examples, the alkene- or alkyne-containing group is a silane comprising a norbornene group. Prior to immobilizing, the method may further comprise applying the copolymer to a surface of the substrate. For example, the copolymer may be applied to a surface of the substrate by applying a copolymer precursor solution to the surface and curing the precursor solution to form the copolymer. The copolymer precursor solution or copolymer may be applied to the substrate using any known surface application technique known to one skilled in the art, for example, flow-through, spin coating, spray coating, dip coating, or ink-jet coating. Following application of the copolymer to the substrate, excess copolymer may be removed through a polishing step (e.g., from interstitial regions of a patterned substrate, leaving copolymer at the patterned regions such as wells).

In some examples, the method of immobilizing the copolymer further comprises functionalizing the substrate with the alkenyl- or alkynyl-containing group prior to immobilizing of the copolymer on the substrate. In some examples, a surface of the substrate is pretreated with an alkene- or alkyne-containing silane. For example, the functionalized silane may be deposited onto the surface by Chemical Vapor Deposition (CVD) method. In some examples, the functionalized silane can be applied onto the first surface by CVD method using Yield Engineering Systems (YES) oven.

In an aspect, there is provided a method of grafting a plurality of oligonucleotides to a copolymer as set defined above by formula (II), (IIa), (IIb), (IIc), (IId), or (IIe) comprising reacting azido groups of the copolymer with the plurality of oligonucleotides. The plurality of oligonucleotides comprise alkenyl or alkynyl groups, and the reaction occurs between the azido groups of the copolymer and the alkenyl or alkynyl groups of the oligonucleotides. The alkene- or alkyne-containing group may be alkenyl, alkynyl, cycloalkenyl, or cycloalkynyl, or a substituted variant thereof. For example, the alkene- or alkyne-containing group comprises cycloalkynyl, for example, bicyclo[6.1.0]non-4-yne (BCN). The alkene- or alkyne-containing group may comprise alkynyl.

The oligonucleotides may be grafted to the copolymer prior to immobilization of the copolymer to a substrate. For example, the oligonucleotides may be grafted to the copolymer after immobilization of the copolymer to the substrate. The alkene- or alkyne-containing groups on the substrate and the oligonucleotide may be the same or different. The method may further comprise a washing step to remove unreacted (ungrafted) oligonucleotides. The method may further comprise a drying step.

In another aspect, there is provided a method of making a compound of formula (I):

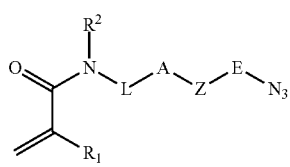

(I)

comprising reacting a compound of Formula (X) with an acrylate of Formula (XI):

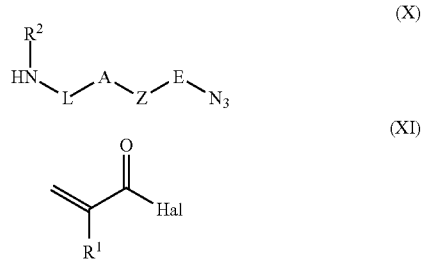

to form the compound of Formula (I); wherein $R^1$, $R^2$, L, A, Z and E are as set out above for formula (I); and Hal is Cl or F.

There is also provided a method of making a compound of Formula (Ik):

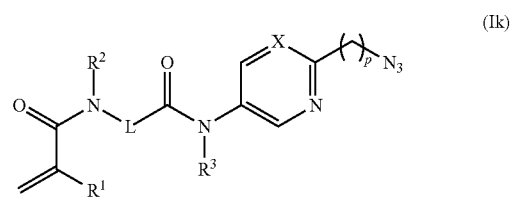

comprising reacting a compound of Formula (Xa):

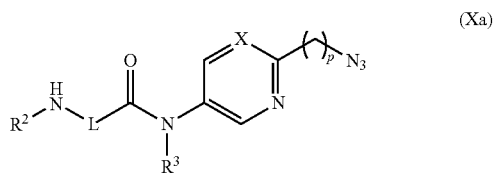

with an acrylate of Formula (XI):

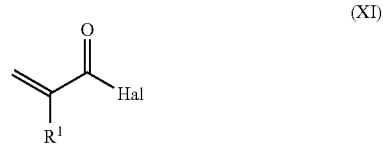

wherein $R^1$, $R^2$, $R^3$, L, X and p are as set out above for formula (I), (Ia) and (Ib); and Hal is Cl or F, to form a compound of Formula (Ij).

The method may further comprise reacting a compound of Formula (XII):

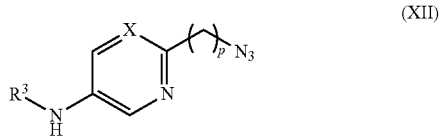

with a compound of Formula (XIII):

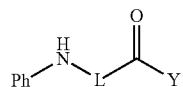
(XIII)

to thereby form the compound of Formula (Xa); wherein $R^3$, X and p are as set out above for formula (I) and formula (Ia); Pg is H or an amino protecting group; and Y is —OH or —Cl.

There is also provided a method of making a compound of Formula (Ik) comprising reacting a compound of Formula (XIV):

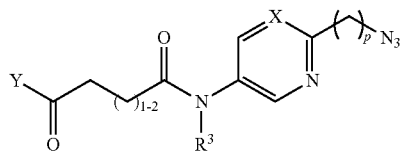
(XIV)

with a compound of Formula (XV):

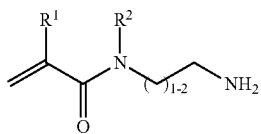
(XV)

to form the compound of Formula (Ik)

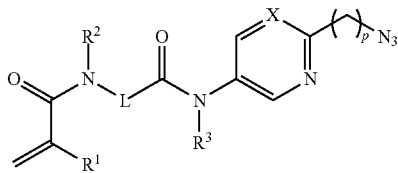
(Ik)

wherein $R^1$, $R^2$, $R^3$, L X and p are as set out above for formula (I), (Ia) and (Ik); Y is —OH or —$C_1$.

The method of making a compound of Formula (XIV) may further comprise reacting a compound of Formula (XII) with a cyclic anhydride (such as succinic or glutaric anhydride) to form the compound of Formula (XIV).

There is also provided a method of forming a compound according to formula (Ie)

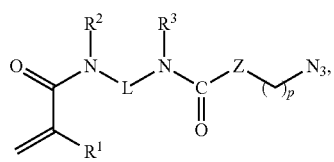
(Ie)

wherein the method comprises reacting a compound of formula (Xb)

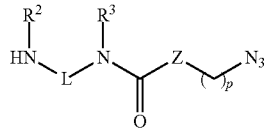
(Xb)

with an acrylate of Formula (XI):

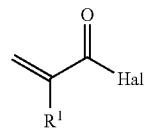
(XI)

wherein $R^1$, $R^2$, $R^3$, L, Z and p are as defined above for formula (I) and formula (Ia); and Hal is Cl or F; to form a compound of Formula (Ie).

The compound according to formula (Xb) may be formed by a method comprising a step of reacting a compound of formula (XVI)

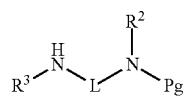
(XVI)

with a compound of formula (XVII)

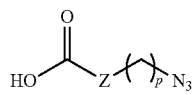
(XVII)

to form the compound of (Xb)

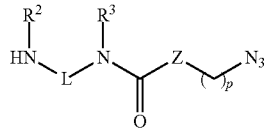
(Xb)

wherein $R^1$, $R^2$, $R^3$, L, Z and p are as defined above for formula (I) and (Ia); Pg is H or an amino protecting group.

Oligonucleotide bound copolymers as described herein may be used in a variety of amplification techniques. Exemplary techniques that can be used include, but are not limited to, polymerase chain reaction (PCR), rolling circle amplification (RCA), multiple displacement amplification (MDA), or random prime amplification (RPA), or a combination thereof. In some examples, one or more primers used for amplification are attached to a copolymer coating on the substrate. Formats that utilize two species of attached primer enable bridge amplification because double stranded amplicons form a bridge-like structure between the two attached primers that flank the template sequence that has been copied. Amplification can also be carried out with one amplification primer attached to a copolymer coating and the second primer in solution (e.g., emulsion PCR), or both primers in solution.

The copolymer-coated substrate described herein can be used in a method for determining a nucleotide sequence of a target nucleic acid. For example, the method comprises:
hybridizing a target nucleic acid to one of a plurality of primers covalently bound to a substrate via a copolymer as described herein (or to the oligonucleotide of recurring monomer unit of Formula (VI), (VIa), (VIb), (VIc), (VId), or (Vie);
amplifying the hybridized target nucleic acid using the plurality of primers to form a cluster of substrate-bound amplicons;
treating the cluster of substrate-bound amplicons with labeled nucleotides and a polymerase such that a detectable signal is generated when a nucleotide is incorporated by the polymerase; and detecting the signal, thereby determining a nucleotide sequence of the target nucleic acid.

Determination of the nucleotide or nucleotides incorporated during each flow step for one or more of the polynucleotides attached to the polymer coating on the surface of the substrate present in a flow cell is achieved by detecting a signal produced at or near the template. In some examples, the detectable signal comprises an optical signal. In other examples, the detectable signal comprises a non-optical signal. In such examples, the non-optical signal comprises a change in pH or electrical current at or near one or more of the nucleic acids being sequenced.

Suitable sequencing methods include, but are not limited to, sequencing-by-synthesis, pyrosequencing, sequencing-by-ligation, and other methods known in the art.

In sequencing-by-synthesis methods, one or more nucleotides are provided to a template polynucleotide that is associated with a polynucleotide polymerase. The polynucleotide polymerase incorporates the one or more nucleotides into a newly synthesized nucleic acid strand that is complementary to the polynucleotide template. The synthesis is initiated from an oligonucleotide primer that is complementary to a portion of the template polynucleotide or to a portion of a universal or non-variable nucleic acid that is covalently bound at one end of the template polynucleotide. As nucleotides are incorporated against the template polynucleotide, a detectable signal is generated that allows for the determination of which nucleotide has been incorporated during each step of the sequencing process. In this way, the sequence of a nucleic acid complementary to at least a portion of the template polynucleotide can be generated, thereby permitting determination of the nucleotide sequence of at least a portion of the template polynucleotide.

Other useful techniques for which the present copolymers and substrates may be used include real-time monitoring of DNA polymerase activity, SBS technologies that detect proton release upon nucleotide incorporation (e.g., Ion Torrent, Thermo Fisher), and gene expression analysis. For example, nucleotide incorporations can be detected through fluorescence resonance energy transfer (FRET) interactions between a fluorophore-bearing polymerase and γ-phosphate-labeled nucleotides, or with zeromode waveguides (ZMWs). Gene expression can be detected or quantified using RNA sequencing techniques, such as those, referred to as digital RNA sequencing. RNA sequencing techniques can be carried out using sequencing methodologies known in the art such as those set forth above. Gene expression can also be detected or quantified using hybridization techniques carried out by direct hybridization to an array or using a multiplex assay, the products of which are detected on an array.

In some examples of the compounds of Formula (I)(Ik), the recurring monomer unit of Formula (II)-(IIe), the recurring monomer unit of Formula (IV)-(IVd), the recurring monomer unit of Formula (V)-(Vd), and the recurring monomer unit of Formula (VI)-(VId), $R^1$ is H. In some examples, $R^1$ is H or methyl. In some examples, $R^1$ is $C_{1-4}$ alkyl. In some examples, $R^1$ is methyl, ethyl, propyl, isopropyl, butyl, isobutyl, sec-butyl, or tert-butyl.

In some examples, $R^2$ is H. In some examples, $R^2$ is H or methyl. In some examples, $R^2$ is $C_{1-4}$ alkyl. In some examples, $R^2$ is methyl, ethyl, propyl, isopropyl, butyl, isobutyl, sec-butyl, or tert-butyl.

In some examples, $R^3$ is H. In some examples, $R^3$ is H or methyl. In some examples, $R^3$ is $C_{1-4}$alkyl. In some examples, $R^3$ is methyl, ethyl, propyl, isopropyl, butyl, isobutyl, sec-butyl, or tert-butyl.

In some examples, X is CH. In some examples, X is N.

In some examples, p is 1. In some examples, p is 1 or 2.

In some examples, L is a linker with a linear chain that is a —$C_{2-20}$ alkylene- or a 3- to 20-atom linear heteroalkylene, each optionally substituted with one or more substituents selected from the group consisting of —$C_{1-4}$ alkyl, —OH, —$OC_{1-4}$ alkyl, or =O. In some examples, L is a linker with a linear chain that is a —$C_{2-6}$ alkylene-, optionally substituted with one or more —$C_{1-4}$alkyl, —OH, —$OC_{1-4}$ alkyl, or =O substituents. In some examples, L is unsubstituted —$C_{2-6}$alkylene- (also drawn as —$(CH_2)_{2-6}$—). In some examples, L is unsubstituted —$C_{3-4}$ alkylene-. In some examples, L is —$(CH_2)_3$—. In some examples, L is —$(CH_2)_4$—.

In some examples, L is a linker with a linear chain that is a 3- to 20-atom linear heteroalkylene, optionally substituted with one or more substituents selected from the group consisting of —$C_{1-4}$ alkyl, —OH, —$OC_{1-4}$ alkyl, or =O. In some examples, L comprises one or more ethylene glycol units. In some examples, L is —$CH_2CH_2(OCH_2CH_2)_x$—$OCH_2CH_2$—, where x is 0 to 10. In some examples, x is 1, 2, 3, 4, 5, or 6. In some examples, L comprises one or more amide groups. In some examples, L is —$C_{2-6}$ alkyl-NHC(O)—$C_{2-6}$ alkyl-. In some examples, L is —$(CH_2)_2$—NHC(O)—$(CH_2)_2$— or —$(CH_2)_3$—NHC(O)—$(CH_2)_2$—. In some examples, L comprises one or more natural or unnatural amino acids. In some examples, L comprises one or more natural amino acids. In some examples, L comprises one or more amino acids selected from the group consisting of glycine, alanine, valine, isoleucine, leucine, lysine, serine, threonine, cysteine, asparagine, or glutamine. In some examples, L comprises 1, 2, or 3 amino acid units.

In some examples, the compound of Formula (Ik) is a compound of Formula (Im). In some examples, the recurring monomer unit of Formula (IIb) is a recurring monomer unit of Formula (IIc). In some examples, the recurring monomer unit of Formula (IVb) is a recurring monomer unit of Formula (IVc). In some examples, the recurring monomer unit of Formula (Vb) is a recurring monomer unit of Formula (Vc). In some examples, the recurring monomer unit of Formula (VIb) is a recurring monomer unit of Formula (Vic). In some examples of each independent formula, $R^1$ is H. In some examples, $R^1$ is H or methyl. In some examples, $R^1$ is $C_{1-4}$alkyl. In some examples, $R^1$ is methyl, ethyl, propyl, isopropyl, butyl, isobutyl, sec-butyl, or tert-butyl.

In some examples, $R^2$ is H. In some examples, $R^2$ is H or methyl. In some examples, $R^2$ is $C_{1-4}$alkyl. In some examples, $R^2$ is methyl, ethyl, propyl, isopropyl, butyl, isobutyl, sec-butyl, or tert-butyl.

In some examples, $R^3$ is H. In some examples, $R^3$ is H or methyl. In some examples, $R^3$ is $C_{1-4}$ alkyl. In some examples, $R^3$ is methyl, ethyl, propyl, isopropyl, butyl, isobutyl, sec-butyl, or tert-butyl.

In some examples, X is CH. In some examples, X is N.

In some examples, n is 1-10, 1-6, or 2, 3, 4, 5, or 6. In some examples, n is 3 or 4.

In some examples, p is 1. In some examples, p is 1 or 2.

In some examples, the ==== of Formula (IV), (IVa), (IVb), (IVc), (IVd), or (IVe) is a single bond. In some examples, it is a double bond. In some examples, the triazole of Formula (IV), (IVa), (IVb), (IVc), (IVd), or (IVe) is covalently bound (directly or indirectly through a linker) through one or both triazole/triazoline ring carbon atoms to the surface.

In some examples of Formula (V), (Va), (Vb), (Vc), (Vd), or (Ve) or of Formula (VI), (VIa), (VIb), (VIc), (VId), or (VIe), G is a linker between the triazole/triazoline ring and the substrate. In some examples, G is a silane linker. In some examples, G is —X'—$R^C$—Si(O—)$_3$, where X' is the product of a reaction of a group X of a silane linker precursor with an azido group of the copolymer. In some examples, X is alkenyl, alkynyl, norbornenyl, or bicyclononynyl. Thus, in some examples, X' is a single bond, a double bond,

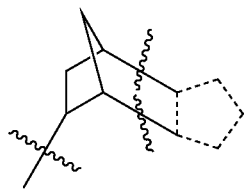

where the dotted 5-membered ring is the triazoline unit, or

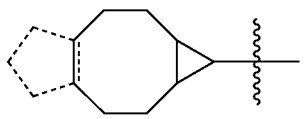

where the dotted 5-membered ring is the triazoline unit. In some examples, G is -cycloalkyl-CH$_2$CH$_2$—Si(O—)$_3$ where the cycloalkyl is fused to the triazoline unit. In some examples, G is -cyclalkenyl-CH$_2$CH$_2$—Si(O—)$_3$ where the cycloalkenyl is fused to and shares the double bond with the triazole unit.

In some examples is a copolymer comprising a recurring monomer unit of Formula (II), Formula (IIa), Formula (IIB), Formula (IIc), Formula (IId), or Formula (IIe) and at least one other recurring monomer unit. The at least one other recurring monomer unit is selected from the group consisting of a polyacrylamide, a polyacrylate, a polyurethane, a polysiloxane, a silicone, a polyacrolein, a polyphosphazene, a polyisocyanate, a poly-ol, and a polysaccharide, and combinations thereof. In some examples, the copolymer comprises a recurring monomer unit of Formula (II), Formula (IIa), Formula (IIb), Formula (IIc), Formula (IId), or Formula (IIe) and a recurring monomer unit of Formula (III). In some examples, the copolymer comprises a recurring monomer unit of Formula (II), Formula (IIa), Formula (IIb), Formula (IIc), Formula (IId), or Formula (IIe), a recurring monomer unit of Formula (III), and at least one other recurring monomer unit as described above.

In some examples of the recurring monomer unit of Formula (III), $R^4$ is H. In some examples, $R^4$ is $C_{1-4}$ alkyl. In some examples, $R^4$ is H or methyl. In some examples, $R^4$ is methyl, ethyl, propyl, isopropyl, butyl, isobutyl, sec-butyl, or tert-butyl.

In some examples, $R^5$ is H. In some examples, $R^5$ is $C_{1-4}$ alkyl. In some examples, $R^5$ is H or methyl. In some examples, $R^5$ is methyl, ethyl, propyl, isopropyl, butyl, isobutyl, sec-butyl, or tert-butyl.

In some examples, $R^6$ is H. In some examples, $R^6$ is $C_{1-4}$ alkyl. In some examples, $R^6$ is H or methyl. In some examples, $R^6$ is methyl, ethyl, propyl, isopropyl, butyl, isobutyl, sec-butyl, or tert-butyl.

Some examples provided in the present application are directed to a substrate having a copolymer as described herein covalently bound to a substrate, where the substrate-bound copolymer comprises a recurring monomer unit of Formula (II), (IIa), (IIb), (IIc), (IId), or (IIe). Thus, in some examples, the substrate-bound copolymer comprises a recurring monomer unit of Formula (II), (IIa), (IIb), (IIc), (IId), or (IIe) and a recurring monomer unit that is covalently bound to the substrate (directly or indirectly via a linker). In some examples, the substrate-bound copolymer comprises a recurring monomer unit of Formula (II), (IIa), (IIb), (IIc), (IId), or (IIe) and a recurring monomer unit of Formula (IVb), (IVc), (IVd), or (IVe):

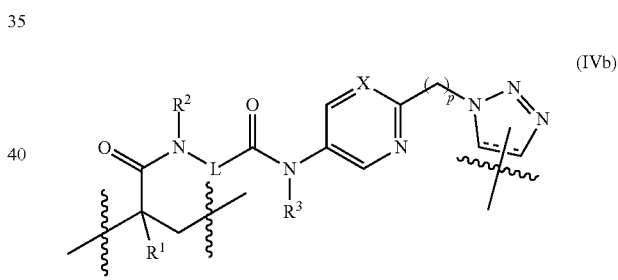

(IVb)

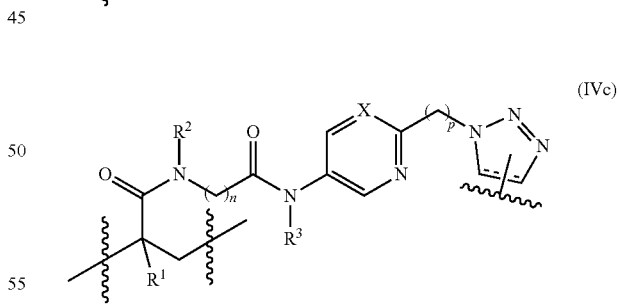

(IVc)

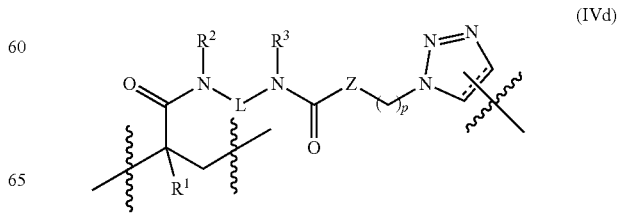

(IVd)

-continued

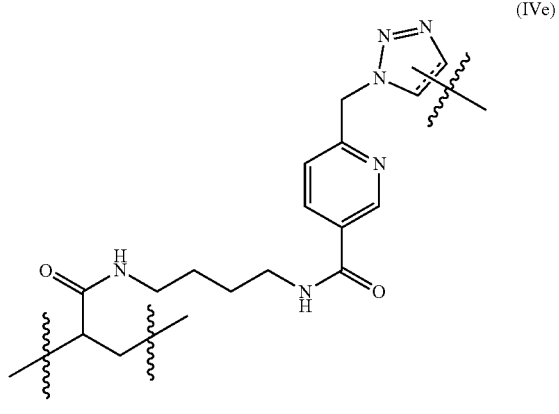
(IVe)

wherein $R^1$, $R^2$, $R^3$, X, L, p, and n are as defined herein, ----- is a single or double bond, and the triazole or triazoline is covalently bound (directly or indirectly through a linker) through one (e.g., where the substrate-bound alkenyl or alkynyl group is acyclic) or both (e.g., where the substrate-bound alkenyl or alkynyl group is part of a ring) triazole/triazoline ring carbon atoms to the substrate.

In some examples, the substrate-bound copolymer comprises a recurring monomer unit of Formula (II), (IIa), (IIb), (IIc), (IId), or (IIe) and a recurring monomer unit of Formula (Vb), (Vc), (Vd), or (Ve):

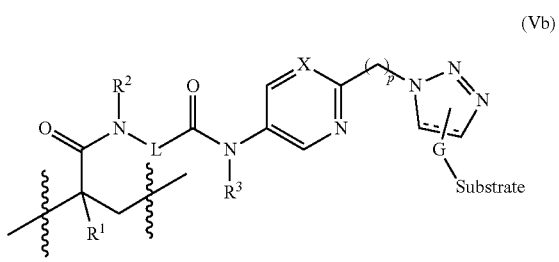
(Vb)

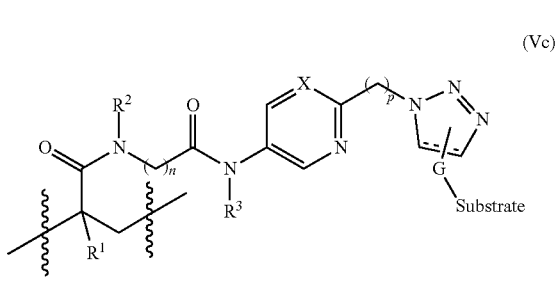
(Vc)

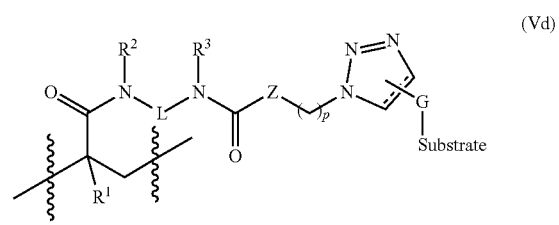
(Vd)

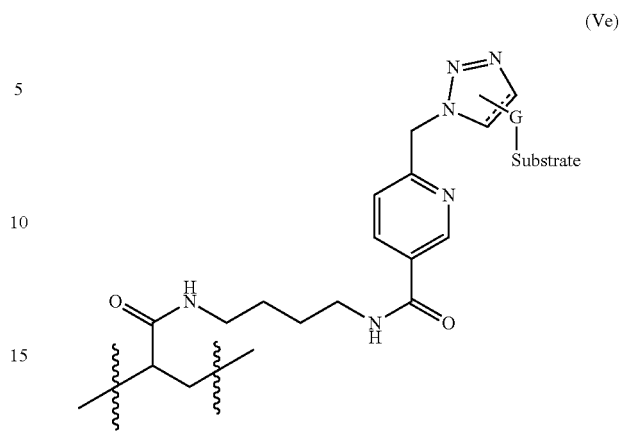
(Ve)

wherein $R^1$, $R^2$, $R^3$, X, n, p, and G are as defined herein.

Described herein is a copolymer comprising a recurring monomer unit of Formula (II), (IIa), (IIb), (IIc), (IId), or (IIe), wherein the copolymer is covalently bound to an oligonucleotide. Thus, in some examples, the oligonucleotide-bound copolymer comprises a recurring monomer unit of Formula (II), (IIa), (IIb), (IIc), (IId), or (IIe) and a recurring monomer unit that is covalently bound to the oligonucleotide. In some examples, the oligonucleotide-bound copolymer comprises a recurring monomer unit of Formula (II), (IIa), (IIb), (IIc), (IId), or (IIe) and a recurring monomer unit of Formula (IV), (IVa), (IVb), (IVc), (IVd), or IV (e), wherein $R^1$, $R^2$, $R^3$, L, p, and n are as defined herein, ----- is a single or double bond, and the copolymer is covalently bound (directly or indirectly through a linker) through one or both triazole/triazoline ring carbon atoms to the oligonucleotide. In some examples, the oligonucleotide-bound copolymer comprises a recurring monomer unit of Formula (II), (IIa), (IIb), (IIc), (IId), or (IIe) and a recurring monomer unit of Formula (VIb), (VIc), (VId), or (VIe):

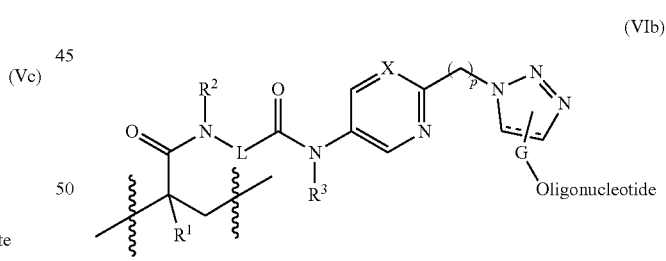
(VIb)

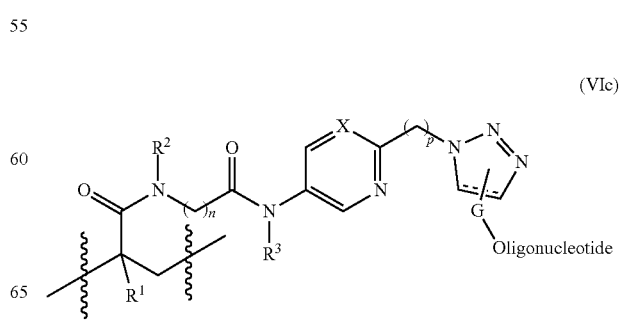
(VIc)

-continued (VId)

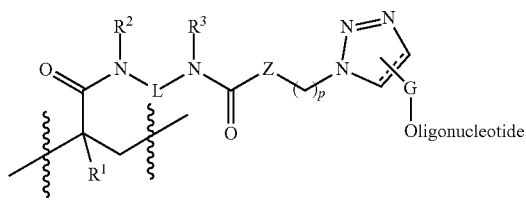

(VIe)

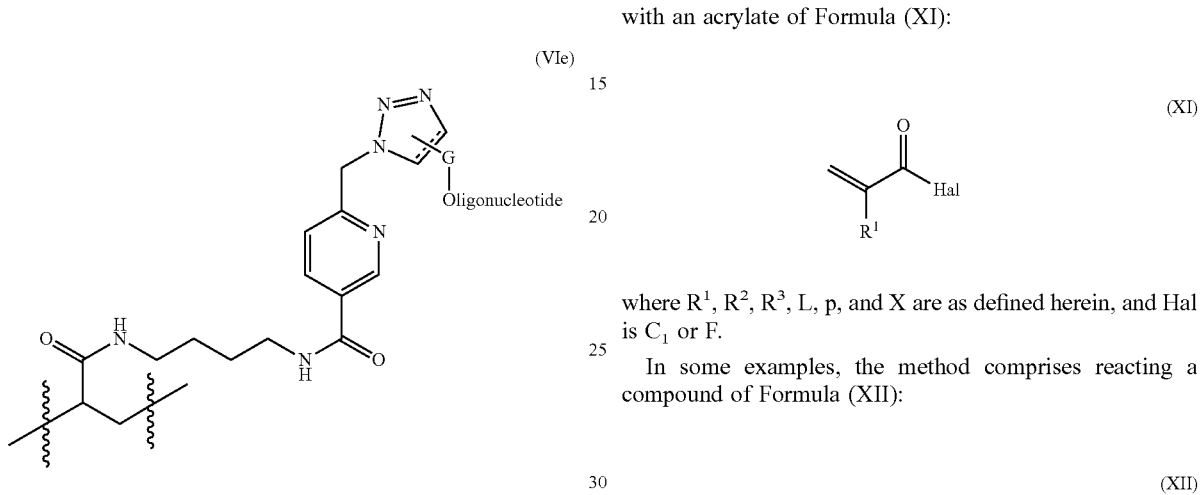

where $R^1$, $R^2$, $R^3$, X. n, p, and G each as defined herein.

In some examples, the attached oligonucleotides are DNA, RNA, genomic DNA, template DNA fragments, or primers such as amplification primers. In some examples, the oligonucleotides are primers. In some examples, the primers are P5 and P7 sequences for use in sequencing-by-synthesis systems.

In some examples, the copolymers described herein are covalently bound to both a substrate and to an oligonucleotide. Thus, in some examples, the copolymer comprises a recurring monomer unit of Formula (II), (IIa), (IIb), (IIc), (IId), or (IIe), a recurring monomer unit of Formula (V), (Va), (Vb), (Vc), (Vd), or (Ve), and a recurring monomer unit of Formula (VI), (VIa), (VIb), (VIc), (VId), or (VIe).

Some examples provided by the present application are directed to methods of making a compound of Formula (Ik), methods of making a copolymer comprising a recurring monomer unit of Formula (IIb), and methods of making a copolymer comprising a recurring monomer unit of Formula (IIb) and a recurring monomer unit of Formula (III).

Described herein is a method of making a compound of Formula (Ik):

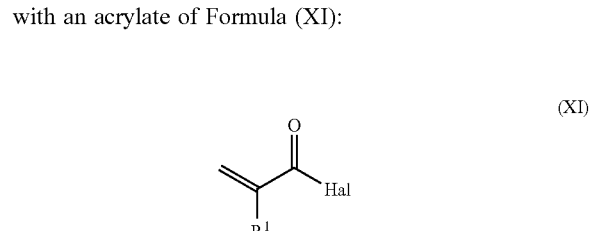

comprising reacting a compound of Formula (Xa):

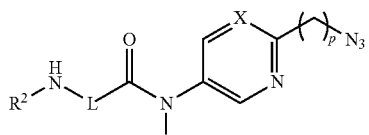

with an acrylate of Formula (XI):

(XI)

where $R^1$, $R^2$, $R^3$, L, p, and X are as defined herein, and Hal is $C_1$ or F.

In some examples, the method comprises reacting a compound of Formula (XII):

(XII)

wherein p, $R^3$, and X are as defined herein;
with a compound of Formula (XIII):

(XIII)

wherein
Pg is H or an amino protecting group; and
Y is —OH or —Cl;
to form the compound of Formula (Xa).

In other aspects is a method of making a compound of Formula (I) comprising reacting a compound of Formula (XIV):

(XIV)

where Y is —OH or —Cl;
with a compound of Formula (XV):

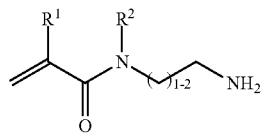

to form the compound of Formula (Ik).

Such method may further comprise reacting a compound of Formula (XII) with a cyclic anhydride (such as succinic or glutaric anhydride) to form the compound of Formula (XIV).

Some examples provided by the present application are directed to a method of immobilizing a copolymer (or oligonucleotide-bound copolymer) as described herein on a substrate comprising reacting an azido group of a copolymer comprising a recurring monomer unit of Formula (II), (IIa), (IIb), (IIc), (IId), or (IIe) with an alkenyl- or alkynyl-containing group on a substrate to form a covalent bond between the copolymer and the substrate. In some examples, the alkene- or alkyne-containing group is alkenyl, alkynyl, or cycloalkynyl, cycloalkenyl. In some examples, the alkene- or alkyne-containing group is norbornenyl. In some examples, the alkene- or alkyne-containing group is a silane. In some examples, the alkene- or alkyne-containing group is a silane comprising a norbornene group. In some examples, prior to immobilizing, the method further comprises applying the copolymer to a surface of the substrate. In other examples, the copolymer is applied to a surface of the substrate by applying a copolymer precursor solution to the surface and curing the precursor solution to form the copolymer. The copolymer precursor solution or copolymer may be applied to the substrate using any known surface application technique known to one skilled in the art, for example, flow-through, spin coating, spray coating, dip coating, or ink-jet coating. In some examples, following applying the copolymer to the substrate, excess copolymer is removed through a polishing step (e.g., from interstitial regions of a patterned substrate, leaving copolymer at the patterned regions such as wells).

In some examples, the method of immobilizing the copolymer further comprises functionalizing the substrate with the alkenyl- or alkynyl-containing group prior to immobilizing of the copolymer on the substrate. In some examples, a surface of the substrate is pretreated with an alkene- or alkyne-containing silane. In some examples, the functionalized silane is deposited onto the surface by Chemical Vapor Deposition (CVD) method. In some such examples, functionalized silane can be applied onto the first surface by CVD method using Yield Engineering Systems (YES) oven.

A method of grafting an oligonucleotide to a copolymer as described herein comprises reacting an azido group of the copolymer with an alkenyl- or alkynyl-containing group on an oligonucleotide to form an oligonucleotide-bound copolymer. In some examples, the alkene- or alkyne-containing group is alkenyl, alkynyl, cycloalkenyl, or cycloalkynyl, or a substituted variant thereof. In some examples, the alkene- or alkyne-containing group comprises cycloalkynyl, for example, bicyclo[6.1.0] non-4-yne (BCN). In some other examples, the alkene- or alkyne-containing group comprises alkynyl. In some examples, oligonucleotides are grafted to the copolymer prior to immobilization of the copolymer to a substrate. In some examples, oligonucleotides are grafted to the copolymer after immobilization of the copolymer to a substrate. The alkene- or alkyne-containing groups on the substrate and the oligonucleotide may be the same or different. In some examples, the method further comprises a washing step to remove unreacted (ungrafted) oligonucleotides. In some examples, the method further comprises a drying step.

Sequencing Applications

Oligonucleotide arrays as described herein may be used in a variety of amplification techniques. Exemplary techniques that can be used include, but are not limited to, polymerase chain reaction (PCR), rolling circle amplification (RCA), multiple displacement amplification (MDA), or random prime amplification (RPA), or a combination thereof. In particular examples, one or more primers used for amplification is attached to a copolymer coating on the substrate. Formats that utilize two species of attached primer enable bridge amplification because double stranded amplicons form a bridge-like structure between the two attached primers that flank the template sequence that has been copied. Amplification can also be carried out with one amplification primer attached to a copolymer coating and the second primer in solution (e.g., emulsion PCR), or both primers in solution.

In some examples, the copolymer-coated substrate described herein can be used in a method for determining a nucleotide sequence of a target nucleic acid. In such examples, the method comprises:

hybridizing a target nucleic acid to one of a plurality of primers covalently bound to a substrate via a copolymer as described herein (or to the oligonucleotide of recurring monomer unit of Formula (VI), (VIa), (VIb), (Vic), (VId), or (VIe);

amplifying the hybridized target nucleic acid using the plurality of primers to form a cluster of substrate-bound amplicons;

treating the cluster of substrate-bound amplicons with labeled nucleotides and a polymerase such that a detectable signal is generated when a nucleotide is incorporated by the polymerase; and detecting the signal, thereby determining a nucleotide sequence of the target nucleic acid.

Determination of the nucleotide or nucleotides incorporated during each flow step for one or more of the polynucleotides attached to the polymer coating on the surface of the substrate present in a flow cell is achieved by detecting a signal produced at or near the template. In some examples, the detectable signal comprises an optical signal. In other examples, the detectable signal comprises a non-optical signal. In such examples, the non-optical signal comprises a change in pH or electrical current at or near one or more of the nucleic acids being sequenced.

Suitable sequencing methods include, but are not limited to, sequencing-by-synthesis, pyrosequencing, sequencing-by-ligation, and other methods known in the art.

In sequencing-by-synthesis, one or more nucleotides are provided to a template polynucleotide that is associated with a polynucleotide polymerase. The polynucleotide polymerase incorporates the one or more nucleotides into a newly synthesized nucleic acid strand that is complementary to the polynucleotide template. The synthesis is initiated from an oligonucleotide primer that is complementary to a portion of the template polynucleotide or to a portion of a universal or non-variable nucleic acid that is covalently bound at one end of the template polynucleotide. As nucleotides are incorporated against the template polynucleotide, a detectable signal is generated that allows for the determination of which nucleotide has been incorporated during each step of the sequencing process. In this way, the sequence of a nucleic acid complementary to at least a portion of the template polynucleotide can be generated, thereby permitting determination of the nucleotide sequence of at least a portion of the template polynucleotide.

Other useful techniques for which the present copolymers and substrates may be used include real-time monitoring of DNA polymerase activity, SBS technologies that detect proton release upon nucleotide incorporation (e.g., Ion Torrent, Thermo Fisher), and gene expression analysis. For example, nucleotide incorporations can be detected through fluorescence resonance energy transfer (FRET) interactions between a fluorophore-bearing polymerase and γ-phosphate-labeled nucleotides, or with zeromode waveguides (ZMWs). Gene expression can be detected or quantified using RNA sequencing techniques, such as those, referred to as digital RNA sequencing. RNA sequencing techniques can be carried out using sequencing methodologies known in the art such as those set forth above. Gene expression can also be detected or quantified using hybridization techniques carried out by direct hybridization to an array or using a multiplex assay, the products of which are detected on an array.

It is to be understood that any respective features/examples of each of the aspects of the disclosure as described herein may be implemented together in any appropriate combination, and that any features/examples from any one or more of these aspects may be implemented together with any of the features of the other aspect(s) as described herein in any appropriate combination.

ADDITIONAL EXAMPLES

Additional examples are disclosed in further detail in the following examples, which are not in any way intended to limit the scope of the claims.

Example 1. 4-Acrylamido-N-(6-(azidomethyl)pyridin-3-yl)butanamide

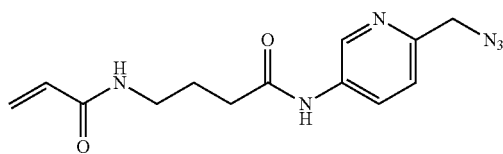 [SMILES: C=CC(=O)NCCCC(=O)Nc1ccc(CN=[N+]=[N-])nc1]

Step 1. tert-Butyl (4-((6-(azidomethyl)pyridin-3-yl)amino)-4-oxobutyl)carbamate. To a solution of 6-(azidomethyl)pyridin-3-amine and 4-((tert-butoxycarbonyl)amino)butanoic acid is added suitable amide coupling reagents (such as EDC/DMAP or EDC/HOBt) in a polar solvent such as dichloromethane or DMF. The resulting mixture is stirred at rt. The product is isolated and purified.

Step 2. 4-Amino-N-(6-(azidomethyl)pyridin-3-yl)butanamide. To a solution of the product from Step 1 in dichloromethane is added TFA. The resulting mixture is stirred at rt (room temperature) to remove the Boc group. The product is isolated and purified.

Step 3. A solution of the product of Step 2 in dichloromethane is treated with acryloyl chloride and Et$_3$N and the resulting mixture is stirred at rt. The product is isolated and purified.

Example 2. 5-Acrylamido-N-(6-(azidomethyl)pyridin-3-yl)pentanamide

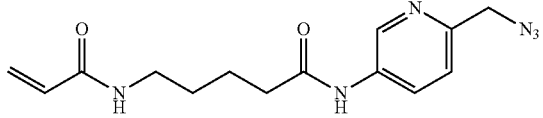 [SMILES: C=CC(=O)NCCCCC(=O)Nc1ccc(CN=[N+]=[N-])nc1]

The title compound is prepared as described for Example 1, using 5-((tert-butoxycarbonyl)amino)pentanoic acid in place of 4-((tert-butoxycarbonyl)amino)butanoic acid.

Example 3. 5-Acrylamido-N-(6-(azidomethyl)pyridin-3-yl)-C$_{6-20}$-alkylamide (z=1, 2, 3, 4, 5, 6, 7, or 8)

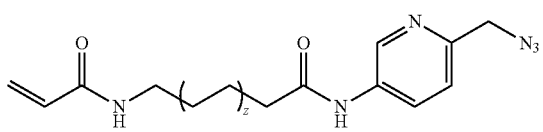

The title compound is prepared as described for Example 1, using the appropriate acid in place of 4-((tert-butoxycarbonyl)amino)butanoic acid.

Example 4. N$^1$-(6-(Azidomethyl)pyridin-3-yl)-N4-(2-methacrylamidoethyl)succinimide

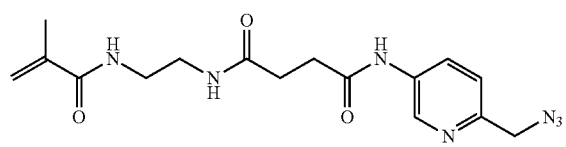 [SMILES: C=C(C)C(=O)NCCNC(=O)CCC(=O)Nc1ccc(CN=[N+]=[N-])nc1]

Step 1. 4-((6-(Azidomethyl)pyridin-3-yl)amino)-4-oxobutanoic acid. A solution of 6-(azidomethyl)pyridin-3-amine and succinic anhydride in dichloromethane is stirred at rt. The product is isolated and purified.

Step 2. To a solution of the product of Step 1 in dichloromethane or DMF is added N-(2-aminoethyl)methacrylamide and suitable amide coupling reagents (such as EDC/DMAP or EDC/HOBt). The resulting mixture is stirred at rt. The product is isolated and purified.

Example 5. N$^1$-(6-(Azidomethyl)pyridin-3-yl)-N4-(3-methacrylamidopropyl)succinimide

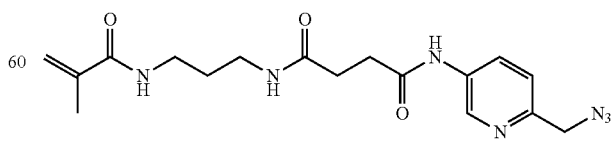

The title compound is prepared as described for Example 4, substituting N-(3-aminopropyl)methacrylamide for N-(2-aminoethyl)methacrylamide.

Example 6

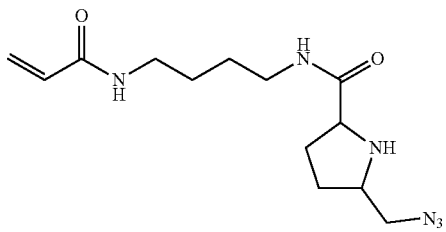 [SMILES: C=CC(=O)NCCCCNC(=O)C1CCC(CN=[N+]=[N-])N1]

Step 1. A solution of 5-hydroxymethyl-L-proline is treated with (PhO)$_2$PON$_3$ in dichloromethane followed by aqueous sodium hydroxide in methanol to form an azido compound, which is isolated and purified.

Step 2. A solution of the product of step 1 and tert-butyloxycarbonyl (tBOC) protected butane-1,4-diamine is treated with thionyl chloride in dicholormethane and the mixture is stirred for one hour at 0° C. The mixture is then treated with trimethylamine in dichloromethane and cooled for 4 hours. The product is isolated and purified.

Step 3. The product of step 2 is treated with a suitable deprotection agent such as trifluoroacetic acid in dichloromethane. The product is then isolated and purified.

Step 4. A solution of the product of Step 3 and acryloyl chloride is treated with aqueous sodium hydroxide at 0° C. for 2 hours, followed by stirring at room temperature for 10 hours. The solution is then treated with aqueous hydrochloric acid and the pH is adjusted to 7. The product is isolated and purified as N-[3-[(1-oxo-2-propen-1-yl)amino]butyl]-5-(azidomethyl)-2-pyrrolidine.

Example 7

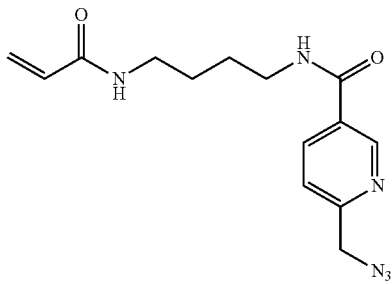 [SMILES: C=CC(=O)NCCCCNC(=O)c1ccc(CN=[N+]=[N-])nc1]

Step 1. A solution of 6-hydroxymethyl-nicotinic acid methyl ester is treated with (PhO)$_2$PON$_3$ in dichloromethane to form an azido compound which is isolated and purified.

Step 2. A solution of the product of step 1 is treated with aqueous sodium hydroxide and ethanol, and is stirred at room temperature for 12 hours. The pH of the mixture is adjusted to 7. The product is isolated and purified.

Step 3. A solution of the product of Step 2 and tert-butyloxycarbonyl (tBOC) protected butane-1,4-diamine is treated with thionyl chloride in dichloromethane and is stirred for one hour at 0° C. The reaction mixture is then treated with trimethylamine in dichloromethane and cooled for 4 hours. The product is isolated and purified.

Step 4. The product of step 3 is treated with a suitable deprotection agent such as trifluoroacetic acid in dichloromethane.

Step 5. A solution of the product of Step 4 and acryloyl chloride is treated with aqueous sodium hydroxide and is stirred for 2 hours at 0° C., the temperature of the reaction mixture is raised to room temperature and the mixture is stirred at room temperature for 10 hours. The solution is then treated with aqueous hydrochloric acid and the pH is adjusted to 7. The product is isolated and purified as N-[3-[(1-oxo-2-propen-1-yl)amino]butyl]-6-(azidomethyl)-3-pyridinecarboxamide.

Example 8

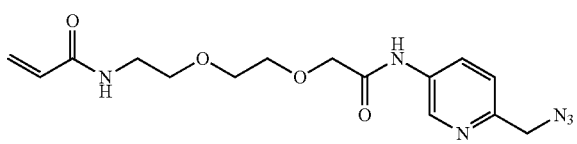 [SMILES: C=CC(=O)NCCOCCOCC(=O)Nc1ccc(CN=[N+]=[N-])nc1]

Step 1. Suitable amide coupling reagents, such as TSTU and N,N-Diisopropylethylamine in DMF, are added to a solution of 4-aminobenzyl alcohol and t-Boc-N-amido-PEG2-CH$_2$CO$_2$H. The resulting mixture is stirred at room temperature and the BOC protected amide is isolated and purified.

Step 2. The product from step 1 is treated with diphenylphosphoryl azide and DBU in DMF, and the resulting mixture is stirred at room temperature.

Step 3. The product of step 2 is deprotected by treatment with a suitable deprotection agent such as trifluoroacetic acid in dichloromethane.

Step 4. A solution of the product of Step 3 is treated with acryloyl chloride in pyridine and the resulting mixture is stirred at 4° C. The product is isolated and purified as

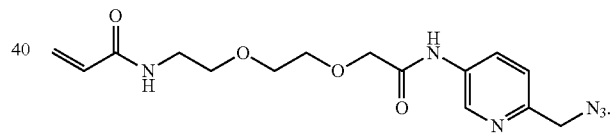

Example 9. Copolymer Generation

A solution of Example 1 (2-50%) and acrylamide is polymerized in the presence of AIBN (or other water-soluble versions, e.g. Vazo 56), or KPS/TMED, or under controlled radical polymerization (CRP) conditions (e.g., RAFT, ATRP, NMP).

Example 10. Immobilization of Copolymers to Substrate

A solution of a copolymer as described herein is applied to a norbornene silane-derivatized substrate surface by spin coating. The substrate is incubated for 1 h at 60° C. to adhere the copolymer to the substrate.

Example 11. Grafting of Copolymers with Oligonucleotides

A copolymer as described in Example 9 or Example 10 is treated with an alkyne-functionalized oligonucleotide, a copper (I) catalyst, and a copper ligand, in aqueous buffer.

The mixture is applied to a substrate surface (e.g., a flow cell channel) and the substrate is incubated and then washed with buffer. The grafting is accomplished with a lower copper loading than grafting with a polymer without the heterocyclic azido units (e.g., alkyl azides, phenyl azides, or benzyl azides). The lower copper loading is advantageous for ease of manufacture (lower toxicity of reagents), reduced DNA damage to grafted oligonucleotides, reduced copper present during downstream amplification and sequencing protocols for reduced damage to template nucleic acids, improved grafting reaction kinetics, and milder grafting conditions, as fast, additive-free reactions are beneficial during complex manufacturing processes.

While various illustrative examples are described above, it will be apparent to one skilled in the art that various changes and modifications may be made therein without departing from the invention. The appended claims are intended to cover all such changes and modifications that fall within the true spirit and scope of the invention.

What is claimed is:

1. A compound of formula (I)

(I)

wherein
R¹ is H or $C_{1-4}$ alkyl;
R² is H or $C_{1-4}$ alkyl;
L is a linker comprising a linear chain having 2 to 20 atoms selected from the group consisting of carbon, oxygen, and nitrogen and optional substituents on the carbon and any nitrogen atoms in the chain;
E is a linear chain having 1 to 4 atoms selected from the group consisting of carbon, oxygen and nitrogen, and optional substituents on the carbon and any nitrogen atoms in the chain;
A is an N substituted amide having formula wherein R³ is H or $C_{1-4}$ alkyl; and
Z is a nitrogen containing heterocycle.

2. The compound according to claim 1, wherein E is optionally substituted $C_{1-4}$ alkylene.

3. The compound according to claim 1, wherein the compound is of formula (Ia)

(Ia)

wherein p is 1, 2, 3 or 4.

4. The compound according to claim 1, wherein the nitrogen containing heterocycle comprises a 6 membered ring.

5. The compound according to claim 4, wherein A and E are bonded at positions 2 and 5 of the 6 membered ring.

6. The compound according to claim 1, wherein the nitrogen containing heterocycle comprises a 5 membered ring.

7. The compound according to claim 1, wherein the nitrogen containing heterocycle is aromatic.

8. The compound according to claim 1, wherein the nitrogen containing heterocycle is saturated.

9. The compound according to claim 1, wherein the compound is of formula (Ib)

(Ib)

wherein X is CH or N; and
wherein p is 1, 2, 3 or 4.

10. The compound according to claim 1, wherein the compound is of formula (Ic)

(Ic)

wherein p is 1, 2, 3 or 4.

11. The compound according to claim 1, wherein the compound is of formula (Id)

(Id)

wherein p is 1, 2, 3 or 4.

12. The compound according to claim 1, wherein the compound is of formula (Ie)

(Ie)

wherein p is 1, 2, 3 or 4.

13. The compound according to claim 1, wherein the compound is of formula (If)

(If)

14. The compound according to claim 1, wherein the compound is of formula (Ig)

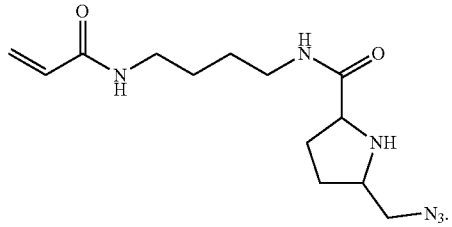

(Ig)

15. The compound according to claim 1, wherein the compound is of formula (Ih)

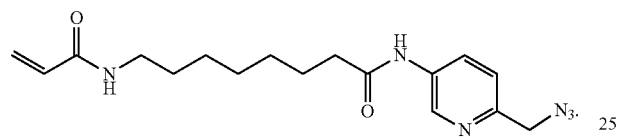

(Ih)

16. The compound according to claim 1, wherein the compound is of formula (Ij)

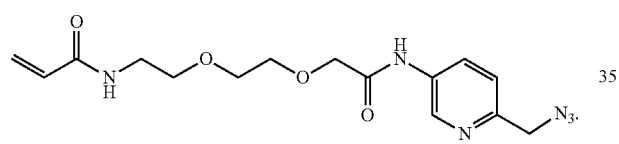

(Ij)

17. The compound according to claim 1, wherein the compound of formula (Ik):

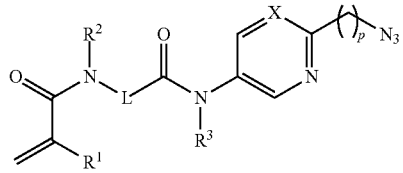

(Ik)

wherein X is CH or N; and
wherein p is 1, 2, 3 or 4.

18. The compound according to claim 17, wherein the compound of Formula (Ik) is a compound of Formula (Im):

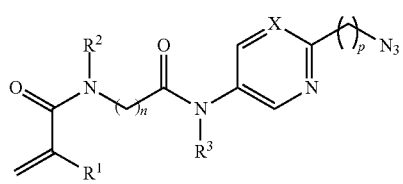

(Im)

wherein n is an integer from 2 to 20; and
wherein p is 1, 2, 3 or 4.

19. A copolymer comprising a recurring monomer unit of formula (II):

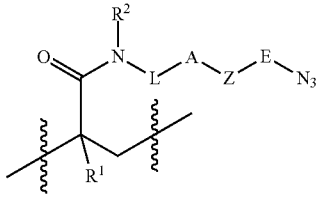

(II)

wherein $R^1$ is H or $C_{1-4}$ alkyl;

$R^2$ is H or $C_{1-4}$ alkyl;

L is a linker comprising a linear chain having 2 to 20 atoms selected from the group consisting of carbon, oxygen, and nitrogen and optional substituents on the carbon and any nitrogen atoms in the chain;

E is a linear chain having 1 to 4 atoms selected from the group consisting of carbon, oxygen and nitrogen, and optional substituents on the carbon and any nitrogen atoms in the chain;

A is an N substituted amide having formula

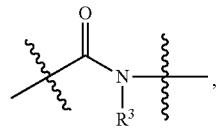

wherein $R^3$ is H or $C_{1-4}$ alkyl; and

Z is a nitrogen containing heterocycle; and at least one other recurring monomer unit.

20. The copolymer according to claim 19, wherein the recurring monomer unit of formula (II) is a recurring monomer unit of formula (IIa)

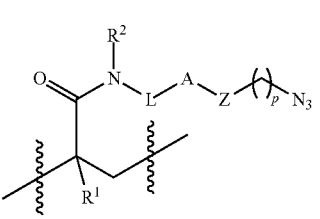

(IIa)

where p is 1, 2, 3, or 4.

* * * * *

```
                          SEQUENCE LISTING

<160> NUMBER OF SEQ ID NOS: 4

<210> SEQ ID NO 1
<211> LENGTH: 29
<212> TYPE: DNA
<213> ORGANISM: Artificial Sequence
<220> FEATURE:
<223> OTHER INFORMATION: Primer

<400> SEQUENCE: 1
aatgatacgg cgaccaccga gauctacac                                      29

<210> SEQ ID NO 2
<211> LENGTH: 24
<212> TYPE: DNA
<213> ORGANISM: Artificial Sequence
<220> FEATURE:
<223> OTHER INFORMATION: Primer

<400> SEQUENCE: 2
caagcagaag acggcatacg agat                                           24

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
aatgatacgg cgaccaccga                                                20

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
caagcagaag acggcatacg a                                              21
```